US006923957B2

(12) United States Patent
Lowery et al.

(10) Patent No.: US 6,923,957 B2
(45) Date of Patent: Aug. 2, 2005

(54) SALMONELLA VACCINE MATERIALS AND METHODS

(75) Inventors: David E. Lowery, Portage, MI (US); Michael J. Kennedy, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 229 days.

(21) Appl. No.: 09/809,524

(22) Filed: Mar. 15, 2001

(65) Prior Publication Data

US 2004/0009191 A1 Jan. 15, 2004

Related U.S. Application Data

(60) Provisional application No. 60/190,178, filed on Mar. 17, 2000.

(51) Int. Cl.[7] .......................... A01N 63/00; A01N 65/00
(52) U.S. Cl. ...................... 424/93.1; 424/93.2; 424/93.4
(58) Field of Search .............................. 424/93.1, 93.2, 424/93.4

(56) References Cited

U.S. PATENT DOCUMENTS

| 4,877,612 A | 10/1989 | Berger et al. |
| 5,876,931 A | 3/1999 | Holden |

FOREIGN PATENT DOCUMENTS

| EP | 109 942 B1 | 3/1991 |
| EP | 180 564 B1 | 7/1991 |
| EP | 231 039 B1 | 1/1992 |
| EP | 0 796 341 B1 | 9/1998 |
| GB | A-2 189 141 | 10/1987 |
| WO | WO 96/17951 | 6/1996 |
| WO | WO 00/14240 | 3/2000 |
| WO | WO 01/47962 A2 | 7/2001 |

OTHER PUBLICATIONS

Cardenas et al., Oral Immunization Using Live Attenuated Salmonella spp. as Carriers of Foreign Antigens, *Clin Microbiol Rev.* 5:328–342 (1992).
Chatfield et al., Live Salmonella as Vaccines and Carriers of Foreign Antigenic Determinants, *Vaccine* 7:495–498 (1989).
Clarke et al., Vaccination of Calves with a Diaminopimelic Acid Mutant of *Salmonella typhimurium*, *Can J Vet Res.* 51:32–38 (1987).
Curtiss et al., Nonrecombinant and Recombinant Avirulent Salmonella Live Vaccines for Poultry, in Blankenship et al., eds., Colonization control of human bacterial enteropathogens in poultry, Academic Press, New York, pp. 169–198 (1991).
Curtiss et al., Recombinant Avirulent Salmonella for Oral Immunization to Induce Mucosal Immunity to Bacterial Pathogens, in Kohler et al., eds., Vaccines: new concepts and developments. Proceedings of the 10th Int'l Convocation of Immunology, Longman Scientific and Technical, Harlow, Essex, UK, pp. 261–271 (1987).
Curtiss, Attenuated Salmonella Strains as Live Vectors for the Expression of Foreign Antigens, in Woodrow et al., eds., New Generation Vaccines, Marcel Dekker, Inc., New York, pp. 161–188 (1990).
Curtiss et al., Live Oral Avirulent Salmonella Vaccines, *Vet. Microbiol.* 37:397–405 (1993).
Curtiss et al., Recombinant Avirulent Salmonella Vaccine Strains with Stable Maintenance and High Level Expression of Cloned Genes in vivo, *Immunol. Invest.* 18:583–596 (1989).
Donnenberg et al., Construction of an eae Deletion Mutant of Enteropathogenic *Escherichia coli* by Using a Positive–Selection Suicide Vector, *Infect. and Immun.* 59:4310–4317 (1991).
Dunyak et al., Identification of Salmonella Pathogenicity Island 2 (SPI2) Genes in *Salmonella choleraesuis* Signature–Tagged Mutagenesis, 97th General Meeting of the American Society for Microbiology, May 4–8, 1997, Miami Beach, Florida, American Society for Microbiology, Washington, D.C. (1997), p. 76. (Abstract).
Galan et al., Cloning and Characterization of the asd gene of *Salmonella typhimurium*: Use in Stable Maintenance of Recombinant Plasmids in Salmonella Vaccine Strains, *Gene* 94:29–35 (1990).
GenBank Accession No. AJ224892, *Salmonella typhimurium* ssaE, sseA, sseB, sscA, sseC, sseD, sseE, sscB, sseF, sseG, ssaG, ssaH, ssaI genes and partial ssaD, ssaJ genes, Hensel, M., 1998.
GenBank Accession No. U51927, *Salmonella typhimurium* SpiR and SpiB genes, partial cds, and SpiC and SpiA genes. complete cds, Groisman, E., 1996.
GenBank Accession No. X99944, *Salmonella typhimurium* ssaQ, ssaR, ssaS, ssaT and ssaU genes, Hensel, M., 1997.
GenBank Accession No. Y09357, *S. typhimurium* ssaJ, ssaK, ssaL, ssaM, ssaV, ssaN, ssaO, ssaP, ssaQ genes, Hensel, M. et al., 1997.
GenBank Accession No. Z95891, *S. typhimurium* ssrA and ssrB genes, Hensel, M., 1998.
Germanier et al., Immunity in Experimental Salmonellosis, II. Basis for the Avirulence and Protective Capacity of gal E Mutants, *Infect. and Immun.* 4:663–673 (1971).
Hensel et al., Analysis of the Boundaries of Salmonella Pathogenicity Island 2 and the Corresponding Chromosomal Region of *Escherichia coli* K–12, *J. Bacteriol.* 179:1105–1111 (1997).
Hensel et al., Functional analysis of ssaJ and ssaK/U operon, 13 genes encoding components of the type III secretion apparatus of Salmonella Pathogenicity Island 2, *Molec. Microbiol.* 24:155–167 (1997).

(Continued)

Primary Examiner—Mark Navarro
(74) Attorney, Agent, or Firm—Pharmacia & Upjohn Company; Thomas A. Wootton

(57) ABSTRACT

Attenuated mutant *Salmonella* bacteria containing inactivated virulence genes are provided for use in safe, efficacious vaccines.

7 Claims, 4 Drawing Sheets

OTHER PUBLICATIONS

Hohmann et al., Intestinal and Serum Antibody Responses in Mice After Oral Immunization with Salmonella, *Escherichia coli*, and *Salmonella–Escherichia coli* Hybrid Strains, *Infect. and Immun.* 25:27–33 (1979).

Hoiseth et al., Aromatic–dependent *Salmonella typhimurium* Are Non–virulent and Effective as Live Vaccines, *Nature* 291:238–239 (1981).

Hone et al., Construction of Defined galE Mutants of Salmonella for Use as Vaccines, *J. Infect. Dis.* 156:167–174 (1987).

Horton et al., Gene Splicing by Overlap Extension: Tailor–Made Genes Using the Polymerase Chain Reaction, *Biotechniques* 8:528–535 (1990).

Kennedy et al., Characterization and Protective Properties of Attenuated Mutants of *Salmonella dublin*, 97th General Meeting of the American Society for Microbiology, B–287:78 (1997.).

Letellier et al., Assessment of various treatments to reduce carriage of Salmonella in swine, *The Canadian Journal of Veterinary Research* 64:27–31 (2000).

Levine et al., Safety, Infectivity, Immunogenicity, and In Vivo Stability of Two Attenuated Auxotrophic Mutant Strains of *Salmonella typhi*, 541Ty and 543Ty, as Live Oral Vaccines in Humans, *J. Clin. Invest.* 79:888–902 (1987).

Lindberg et al., Antibody Response and Protection against Challenge in Mice Vaccinated Intraperitoneally with a Live aroA O4–O9 Hybrid *Salmonella dublin* Strain, *Infect. and Immun.* 61:1211–1221 (1993).

Linde et al., Stable Salmonella Live Vaccine Strains with Two or More Attenuating Mutations and Any Desired Level of Attenuation, *Vaccine* 8:278–282 (1990).

McFarland et al., Effect of Different Purine Auxotrophic Mutations on Mouse–Virulence of a Vi–Positive Strain of *Salmonella dublin* and Two Strains of *Salmonella typhimurium*, *Microb. Pathogen.* 3:129–141 (1987).

Mills et al., A 40kb Chromosomal Fragment Encoding *Salmonella typhimurium* Invasion Genes Is Absent from the Corresponding Region of the *Escherichia coli* K–12 Chromosome, *Mol. Microbiol.* 5:749–759 (1995).

Nnalue et al., Some galE Mutants of *Salmonella choleraesuis* Retain Virulence, *Infect. and Immun.* 54:635–640 (1986).

Nnalue et al., Tests of the Virulence and Live–Vaccine Efficacy of Auxotrophic and galE Derivatives of *Salmonella choleraesuis*, *Infect. and Immun.* 55:955–962 (1987).

O'Callaghan et al., Characterization of Aromatic– and Purine–Dependent *Salmonella typhimurium:* Attenuation, Persistence, and Ability to Induce Protective Immunity in BALB/c Mice, *Infect. and Immun.* 56: 419–423 (1988).

O'Callaghan et al., Immune Responses in BALB/c Mice Following Immunization with Aromatic Compound or Purine–Dependent *Salmonella typhimurium* Strains, *Immunology* 69:184–189 (1990).

Ochman et al., Identification of a pathogenicity island required for Salmonella survival in host cells, *Proc. Natl. Acad. Sci. (USA)* 93:7800–7804 (1996).

Reyrat et al., Counterselectable Markers: Untapped Tools for Bacterial Genetics and Pathogenesis, *Infect. and Immun.* 66:4011–4017 (1998).

Robertsson et al., *Salmonella typhimurium* Infection in Calves: Protection and Survival of Virulent Challenge Bacteria After Immunization with Live or Inactivated Vaccines, *Infect. and Immun.* 41:742–750 (1983).

Shea et al., Identification of a virulence locus encoding a second type III secretion system in *Salmonella typhimurium*, *Proc. Natl. Acad. Sci. (USA)* 93:2593–2597 (1996).

Smith et al., Vaccination of Calves with Orally Administered Aromatic–Dependent *Salmonella dublin*, *Am. J. Vet. Res.* 54:1249–1255 (1993).

Smith et al., Aromatic–dependent *Salmonella typhimurium* as Modified Live Vaccines for Calves, *Am. J. Vet. Res.* 45:59–66 (1984).

Smith et al., Aromatic–dependent *Salmonella dublin* as a Parenteral Modified Live Vaccine for Calves, *Am. J. Vet. Res.* 45:2231–2235 (1984).

Tacket et al., Comparison of the Safety and Immunogenicity of ΔaroC ΔaroD and Δcya Δcrp *Salmonella typhi* Strains in Adult Volunteers, *Infect. and Immun.* 60:536–541 (1992).

Zhang et al., An RNA Helicase, RHIV–1, Induced by Porcine Reproductive and Respiratory Syndrome Virus (PRRSV) is Mapped on Porcine Chromosome 10q13, *Microb. Pathogen.* 28:267–278(2000)..

SEQUENCE LISTING

<160> NUMBER OF SEQ ID NOS: 30

<210> SEQ ID NO 1
<211> LENGTH: 779
<212> TYPE: DNA
<213> ORGANISM: Salmonella dublin

<400> SEQUENCE: 1

-continued

```
atggcacaac aggtaaatga gtggcttatt gcattggctg tggctttat tcgaccatta        60 agcctttctt tattacttcc cctattaaaa agtggcagtt tagggccgc tcttttacgt       120 aatggcgtgc ttatgtcact tacctttccc atattaccaa tcatttacca gcagaagatt      180
atgatgcata ttggtaaaga ttacagttgg ttagggttag tcaccggaga ggtgattatt      240
ggttttttaa ttgggttttg tgcggcggtt cccttttggg ccgttgatat ggcggggttt      300
ctgcttgata ctttacgtgg cgcgacaatg ggtacgatat tcaattctac aatagaagct     360
gaaacctcac tttttggctt gcttttcagc cagttttgt gtgttatttt ctttataagc       420
ggcggcatgg agtttatatt aaacattctg tatgagtcat atcaatattt accaccaggg      480
cgtactttat tatttgaccg gcaattttta aaatatatcc aggcagagtg gagaacgctt      540
tatcaattat gtgtcagttt ctctcttcct gccataatat gtatggtatt agccgatctg     600
gctttaggtc ttttaaatcg gtcggcacaa caattgaatg tgttttttctt ctcaatgccg     660 ctcaaaagta tattggttct actgacgctc ctgatctcat tcccttatgc tcttcatcac     720
tatttggttg aaagcgataa attttatatt tatctaaaag actggtttcc atctgtatg      779
```

<210> SEQ ID NO 2
<211> LENGTH: 779
<212> TYPE: DNA
<213> ORGANISM: Salmonella typhimurium

<400> SEQUENCE: 2

```
atggcacaac aggtaaatga gtggcttatt gcattggctg tggctttat tcgaccattg        60 agcctttctt tattacttcc cttattaaaa agtggcagtt tagggccgc acttttacgt       120 aatggcgtgc ttatgtcact tacctttccg atattaccaa tcatttacca gcagaagatt      180
atgatgcata ttggtaaaga ttacagttgg ttagggttag tcactggaga ggtgattatt      240 ggttttttcaa ttgggttttg tgcggcggtt cccttttggg ccgttgatat ggcggggttt     300
ctgcttgata ctttacgtgg cgcgacaatg ggtacgatat tcaattctac aatagaagct     360
gaaacctcac tttttggctt gcttttcagc cagttcttgt gtgttatttt ctttataagc      420
ggcggcatgg agtttatatt aaacattctg tatgagtcat atcaatattt accaccaggg      480
cgtactttat tatttgacca gcaattttta aaatatatcc aggcagagtg gagaacgctt      540
tatcaattat gtatcagctt ctctcttcct gccataatat gtatggtatt agccgatctg     600
gctttaggtc ttttaaatcg gtcggcacaa caattgaatg tgttttttctt ctcaatgccg     660 ctcaaaagta tattggttct actgacgctc ctgatctcat tcccttatgc tcttcatcac     720
tatttggttg aaagcgataa attttatatt tatctaaaag actggtttcc atctgtatg      779
```

<210> SEQ ID NO 3
<211> LENGTH: 749
<212> TYPE: DNA
<213> ORGANISM: Salmonella dublin

<400> SEQUENCE: 3

```
atgaaggttc atcgtatagt atttcttact gtccttacgt tctttcttac ggcatgtgat        60
gtggatcttt atcgctcatt gccagaggat gaggcgaatc aaatgctggc attacttatg       120
cagcatcata ttgatgcgga aaaaaaacag gaagaggacg tgttaccttt acgtgtcgag      180
cagtcgcagt ttattaatgc ggttgagcta cttagactta acggttatcc gcatcgtcag     240
tttacaacgg cggataagat gtttccggct aatcagttag tggtatcacc ccaggaagaa     300
```

```
cagcagaaga ttaattttt  aaaagaacaa agaattgaag gagtgctgag tcagatggag    360
ggcgtgatta atgcaaaagt gaccattgcg ctaccgactt atgatgaggg aagtaacgct    420
tctccgagct cagttgccgt atttataaaa tattcaccac aggtcaatat ggaggccttt    480
cgggtaaaaa ttaaggattt aatagagatg tcaatccctg ggttgcaata cagtaagatt    540
agtatcttga tgcagcctgc tgaattcaga atggtagctg acgtacccgc gagacaaaca    600
ttctggatta tggacgttat caacgccaat aaagggaagg tggagaagtg gttgatgaaa    660 taccccttatc agttgatgtt attgttgaca ggactgttat taggagtggg catcctgatc    720
ggctattttt gcctgagacg ccgttttttg                                      749

<210> SEQ ID NO 4
<211> LENGTH: 749
<212> TYPE: DNA
<213> ORGANISM: Salmonella typhimurium

<400> SEQUENCE: 4
atgaaggttc atcgtatagt atttcttact gtccttacgt tctttcttac ggcatgtgat     60
gtggatcttt atcgctcatt gccagaagat gaagcgaatc aaatgctggc attacttatg    120
cagcatcata ttgatgcgga aaaaaaacag gaagaggatg tgtaacctt acgtgtcgag    180 cagtcgcagt ttattaatgc ggttgagcta cttagactta acggttatcc gcataggcag    240
tttacaacgg cggataagat gtttccggct aatcagttag tggtatcacc ccaggaagaa    300
cagcagaaga ttaattttt aaaagaacaa agaattgaag gaatgctgag tcagatggag    360
ggcgtgatta atgcaaaagt gaccattgcg ctaccgactt atgatgaggg aagtaacgct    420
tctccgagct cagttgccgt atttataaaa tattcacctc aggtcaatat ggaggccttt    480
cgggtaaaaa ttaaagattt aatagagatg tcaatccctg ggttgcaata cagtaagatt    540
agtatcttga tgcagcctgc tgaattcaga atggtagctg acgtacccgc gagacaaaca    600
ttctggatta tggacgttat caacgccaat aaagggaagg tggtgaagtg gttgatgaaa    660 taccccttatc cgttgatgtt atcgttgaca ggactgttat taggagtggg catcctgatc    720
ggctattttt gcctgagacg ccgttttttg                                      749

<210> SEQ ID NO 5
<211> LENGTH: 1052
<212> TYPE: DNA
<213> ORGANISM: Salmonella dublin

<400> SEQUENCE: 5
atggtagtaa ataaacgttt aatcttaatt ttactatta tactcaatac agcaaagagt     60
gatgagttat catggaaagg taatgacttc acccttatg ccagacaaat gccattagca    120
gaggttttac atctgctctc agagaactat gatacggcta ttactattag cccattgata    180
acagctacat ttagtggaaa aattccgcct ggaccaccgg tcgatatttt gaataacctg    240
gcagcacaat atgatttgct tacctggttt gatggcagca tgttatatgt atatcctgca    300
tcgttattaa acatcaggt tatcactttc aatatttttat ctactggacg gttcattcat    360
tacttacgca gccagaatat cctttcatca ccgggatgcg aggttaaaga aattaccggt    420
accaaagctg tggaggtgag cggtgttccc agctgcctga ctcgtattag tcaattagct    480
tcagtgctgg ataatgcgtt aatcaaacga aaagacagtg cggtgagtgt aagtatatac    540
acgcttaagt atgccactgc gatggatacc caataccaat atcgcgatca gtccgtcgtg    600
gttccagggg tcgtgagtgt attgcgtgag atgagtaaaa ccagcgtacc ggcgtcatcg    660
```

```
acgaacaatg gttcacccgc tacacaggca ttgcccatgt ttgctgccga cccacgccag    720
aatgcagtga tcgttcgtga ttatgcggcc aatatggccg ggtatcggaa acttatcaca    780
gaattagatc aacgccagca gatgatagag atttcggtga aaattatcga tgttaatgct    840
ggagatatta accagttagg catcgactgg ggaacggcag tgtcgctggg tggcaagaaa    900
attgcgttca atacaggttt gaatgacggt ggtgctagcg gttttttcaa cggtaatcag    960
cgatacctca aactttatgg tgcgtttgaa tgccctggaa aaaagctctc aggcttatgt   1020
actttcccag ccatctgtgg tgactttaaa ta                                 1052

<210> SEQ ID NO 6
<211> LENGTH: 1052
<212> TYPE: DNA
<213> ORGANISM: Salmonella typhimurium

<400> SEQUENCE: 6
atggtagtaa ataaacgttt aatcttaatt ttactattta tactcaatac agcaaagagt     60
gatgagttat catggaaagg taatgacttc ccctttatg ccagacaaat gccattagca    120
gaggttttac atctgctctc agagaactat gatacggcta ttactattag cccattgata    180
acagctacat ttagtggaaa aattccgcct ggaccaccgg tcgatatttt gaataacctg    240
gcagcacaat atgatttgct tacctggttt gatggcagca tgttatatgt atatcctgca    300
tcgttattaa acatcaggt tatcactttc aatatttat ctactggacg gttcattcat    360
tacttacgca gccagaatat cctttcatca ccgggatgcg aggttaaaga aattaccggt    420
accaaagctg tggaggtgag cggtgttccc agctgcctga ctcgtattag tcaattagct    480
tcagtgctgg ataatgcgtt aatcaaacga aagacagtg cggtgagtgt aagtatatac    540
acgcttaagt atgccactgc gatggatacc cagtaccaat atcgcgatca gtccgtcgtg    600
gttccagggg tcgttagtgt attgcgtgag atgagtaaaa ccagcgtccc gacgtcatcg    660
acgaacaatg gttcacccgc tacacaggca ttgcccatgt ttgctgccga cccacgccag    720
aatgcagtga tcgttcgtga ttatgcggcc aatatggccg ggtatcggaa actcatcaca    780
gaattagatc aacgccagca gatgatagag atttcggtga aaattatcga tgttaatgct    840
ggagatatta accagttagg catcgactgg ggaacggcag tgtcgctggg tggcaagaaa    900
attgcgttca atacaggttt gaatgacggt ggtgctagtg gttttttcaa cggtaatcag    960
cgatacctca aactttatgg tgcgtctgaa tgccctggaa aaaagctctc aggcttatgt   1020
actttcccag ccatctgtgg tgactttaaa ta                                 1052

<210> SEQ ID NO 7
<211> LENGTH: 368
<212> TYPE: DNA
<213> ORGANISM: Salmonella typhimurium

<400> SEQUENCE: 7
atggattggg atctcattac tgaacgtaat attcagcttt ttattcaatt agcaggatta     60
gctgaacggc ctttagcaac caatatgttc tggcggcaag acaatatga aacctatcta    120 aactatcata acggtcgtat tcacttatgt cagatactca agcaaacctt cttagacgaa    180
gaactgcttt ttaaagcgtt ggctaactgg aaacccgcag cgttccaggg tattcctcaa    240
cgattatttt tgttgcgcga tgggcttgca atgagttgtt ctccacctct ttccagctcc    300
gccgagctct ggttacgatt acatcatcga caaataaaat ttctggagtc gcaatgcgtt    360
```

-continued catggtta                                                            368

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 8 tggctttat tcgaccattg agcctttc                                        28

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 9
tttatcgctt tcaaccaaat agtgatg                                        27

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 10
gccaatctag aaattatttt cggaatttga taaa                                34

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 11
aggctgttct gttttctcgc tcacattcaa ccatgctctc caattcgta                49

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 12
tacgaattgg agagcatggt tgaatgtgag cgagaaaaca gaacagcct                49

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 13
gccaatctag atctttcta atcttataat attg                                 34

<210> SEQ ID NO 14
<211> LENGTH: 34
<212> TYPE: DNA
<213> ORGANISM: Artificial Sequence

```
<220> FEATURE:
<223> OTHER INFORMATION: Description of Artificial Sequence: primer

<400> SEQUENCE: 14
gccaatctag actgcagaac cgagccagga gcaa                                    34

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 15
cacctcggga tcaggtcggc tcataaaaaa ttaatcttct gctgtt                       46

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 16
aacagcagaa gattaatttt ttatgagccg acctgatccc gaggtg                       46

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 17
gccaatctag agaagataat ctcggtaaga gaagt                                   35

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 18
gccaatctag attcaaattg taagttttta tgtcaat                                 37

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 19
tttatccagc acagcctgga tattacattt tatacccccac ccgaataaag                  50

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 20
ttattcgggt ggggtataaa atgtaatatc caggctgtgc tg                           42
```

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 21
gccaatctag attcccggca tcaacaaata aact                               34

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 22
gccaagtcga catagtaggt gttctgtggg caata                              35

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 23
ttctggatta tagctattat gattgtttga taagtgattg agtcctga                48

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 24
tcaggactca atcacttatc aaacaatcat aatagctata atccagaa                48

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 25
gccaagtcga cgtgtacgaa caggcttcag tggat                              35

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 26
gccaatctag atcaggcatt agaaatagcg cgtta                              35

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: primer

```
<400> SEQUENCE: 27 attttttaata tacgattaaa cgctcaaaca ttttgccttc ttcaaaga            48

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 28
tctttgaaga aggcaaaatg tttgagcgtt taatcgtata ttaaaaat             48

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 29
gccaatctag atgctcctga ctcagacgac gctgg                          35

<210> SEQ ID NO 30
<211> LENGTH: 368
<212> TYPE: DNA
<213> ORGANISM: S. dublin ssaM

<400> SEQUENCE: 30
atggattggg atctcattac tgaacgtaat attcagcttt ttattcaatt agcaggatta    60
gctgaacggc ctttagcgac caatatgttc tggcggcaag gacaatatga aacctatcta   120
aactatcata acgtcgtat tcacttatgt cagatactca agcaaacctt cttagacgaa    180
gaactgcttt ttaaagcgtt ggctaactgg aaactcgcag cgttccaggg tattcctcaa   240
cgattatttt tgttgcgcga tgggcttgca atgagttgtt ctccacctct ttccagctcc   300
gccgagctct ggttacgatt acatcatcga caaataaaat ttctggagtc gcaatgcgtt   360
catggtta                                                           368
```

SALMONELLA VACCINE MATERIALS AND METHODS

The present invention claims priority of U.S. provisional application No. 60/190,178 filed Mar. 17, 2000, the entire disclosure of which is incorporated by reference herein.

FIELD OF THE INVENTION

The present invention relates generally to genetically engineered salmonellae, which are useful as live vaccines.

BACKGROUND OF THE INVENTION

Diseases caused by *Salmonella* bacteria range from a mild, self-limiting diarrhea to serious gastrointestinal and septicemic disease in humans and animals. *Salmonella* is a gram-negative, rod-shaped, motile bacterium (nonmotile exceptions include *S. gallinarum* and *S. pullorum*) that is non-spore forming. Environmental sources of the organism include water, soil, insects, factory surfaces, kitchen surfaces, animal feces, raw meats, raw poultry, and raw seafoods.

*Salmonella* infection is a widespread occurrence in animals, especially in poultry and swine, and is one of the most economically damaging of the enteric and septicemic diseases that affect food producing animals. Although many serotypes of *Salmonella* have been isolated from animals, *S. chloeraesuis* and *S. typhimurium* are the two most frequently isolated serotypes associated with clinical salmonellosis in pigs. In swine, *S. typhimurium* typically causes an enteric disease, while *S. choleraesuis* (which is host-adapted to swine) is often the etiologic agent of a fatal septicemic disease with little involvement of the intestinal tract. *S. dublin* and *S. typhimurium* are common causes of infection in cattle; of these, *S. dublin* is host adapted to cattle and is often the etiologic agent of a fatal septicemic disease. Other serotypes such as *S. gallinarum* and *S. pullorum* are important etiologic agents of salmonellosis in avian and other species. Although these serotypes primarily infect animals, *S. dublin* and *S. chloeraesuis* also often cause human disease.

Various *Salmonella* species have been isolated from the outside of egg shells, including *S. enteritidis* which may even be present inside the egg yolk. It has been suggested that the presence of the organism in the yolk is due to transmission from the infected layer hen prior to shell deposition. Foods other than eggs have also caused outbreaks of *S. enteritidis* disease in humans.

*S. typhi* and *S. paratyphi* A, B, and C produce typhoid and typhoid-like fever in humans. Although the initial infection with *salmonella* typically occurs through the gastrointestinal tract, typhoid fever is a systemic disease that spreads throughout the host and can infect multiple organ sites. The fatality rate of typhoid fever can be as high as 10% (compared to less than 1% for most forms of salmonellosis). *S. dublin* has a 15% mortality rate when the organism causes septicemia in the elderly, and *S. enteritidis* has an approximately 3.6% mortality rate in hospital/nursing home outbreaks, with the elderly being particularly affected.

Numerous attempts have been made to protect humans and animals by immunization with a variety of vaccines. Many of the vaccines provide only poor to moderate protection and require large doses to be completely efficacious. Previously used vaccines against *salmonellae* and other infectious agents have generally fallen into four categories: (i) specific components from the etiologic agent, including cell fractions or lysates, intact antigens, fragments thereof, or synthetic analogs of naturally occurring antigens or epitopes (often referred to as subunit vaccines); (ii) antiidiotypic antibodies; (iii) the whole killed etiologic agent (often referred to as killed vaccines); or (iv) an avirulent (attenuated) derivative of the etiologic agent used as a live vaccine.

Reports in the literature have shown that attenuated live vaccines are more efficacious than killed vaccines or subunit vaccines for inducing protective immunity. Despite this, high doses of live vaccines are often required for efficacy and few live-attenuated *Salmonella* vaccines are commercially available. Ideally, an effective attenuated live vaccine retains the ability to infect the host without causing serious disease and is also capable of stimulating humoral (antibody-based) immunity and cell-mediated immunity sufficient to provide resistance to any future infection by virulent bacteria.

Several attenuation strategies have been utilized to render *Salmonella* avirulent [Cardenas et al., Clin Microbial Rev. 5:328–342 (1992); Chatfield et al., Vaccine 7:495–498 (1989); Curtiss, in Woodrow et al., eds., New Generation Vaccines, Marcel Dekker, Inc., New York, p. 161 (1990); Curtiss et al., in Kohler et al., eds., Vaccines: new concepts and developments. Proceedings of the 10th Int'l Convocation of Immunology, Longman Scientific and Technical, Harlow, Essex, UK, pp. 261–271 (1987); Curtiss et al., in Blankenship et al., eds., Colonization control of human bacterial enteropathogens in poultry, Academic Press, New York, pp. 169–198 (1991)]. These strategies include the use of temperature sensitive mutants [e.g., Germanier et al., Infect Immun. 4:663–673 (1971)], aromatic and auxotrophic mutants (e.g., -aroA, -asd, -cys, or -thy [Galan et al., Gene 94:29–35 (1990); Hoiseth et al., Nature 291:238–239 (1981); Robertsson et al., Infect Immun. 41:742–750 (1983); Smith et al., Am J Vet Res. 45:59–66 (1984); Smith et al., Am J Vet Res. 45:2231–2235 (1984)]), mutants defective in purine or diaminopimelic acid biosynthesis (e.g., Δpur and Δdap [Clarke et al., Can J Vet Res. 51:32–38 (1987); McFarland et al., Microb Pathog. 3:129–141 (1987); O'Callaghan et al., Infect Immun. 56:419–423 (1988)]), strains altered in the utilization or synthesis of carbohydrates (e.g., ΔgalE [Germanier et al., Infect Immun. 4:663–673 (1971); Hone et al., J Infect Dis. 156:167–174 (1987)]), strains altered in the ability to synthesize lipopolysaccharide (e.g., galE, pmi, rfa) or cured of the virulence plasmid, strains with mutations in one or more virulence genes (e.g., invA) and mutants altered in global gene expression (e.g., -cya -crp, ompR or -phoP [Curtiss (1990), supra; Curtiss et al. (1987), supra; Curtiss et al. (1991)], supra).

In addition, random mutagenesis techniques have been used to identify virulence genes expressed during infection in an animal model. For example, using a variety of approaches, random mutagenesis is carried out on bacteria followed by evaluation of the mutants in animal models or tissue culture systems, such as Signature-Tagged Mutagenesis (STM) [see U.S. Pat. No. 5,876,931].

However, published reports have shown that attempts to attenuate *Salmonella* by these and other methods have led to varying degrees of success and demonstrated differences in both virulence and immunogenicity [Chatfield et al., Vaccine 7:495–498 (1989); Clarke et al., Can J Vet Res. 51:32–38 (1987); Curtiss (1990), supra; Curtiss et al. (1987), supra; Curtiss et al. (1991), supra]. Prior attempts to use attenuation methodologies to provide safe and efficacious live vaccines have encountered a number of problems.

First, an attenuated strain of *Salmonella* that exhibits partial or complete reduction in virulence may not retain the ability to induce a protective immune response when given as a vaccine. For instance, ΔaroA mutants and galE mutants of S. typhimurium lacking UDP-galactose epimerase activity were found to be immunogenic in mice [Germanier et al., Infect Immun. 4:663–673 (1971), Hohmann et al., Infect Immun. 25:27–33 (1979); Hoiseth et al., Nature, 291:238–239 (1981); Hone et al., J. Infect Dis. 156:167–174 (1987)] whereas Δasd, Δthy, and Δpur mutants of S. typhimurium were not [Curtiss et al. (1987), supra, Nnalue et al., Infect Immun. 55:955–962 (1987)]. All of these strains, nonetheless, were attenuated for mice when given orally or parenterally in doses sufficient to kill mice with the wild-type parent strain. Similarly, ΔaroA, Δasd, Δthy, and Δpur mutants of S. chloeraesuis were avirulent in mice, but only ΔaroA mutants were sufficiently avirulent and none were effective as live vaccines [Nnalue et al., Infect Immun. 54:635–640 (1986); Nnalue et al., Infect Immun. 55:955–962 (1987)].

Second, attenuated strains of S. dublin carrying mutations in phoP, phoP crp, [crp-cdt] cya, crp cya were found to be immunogenic in mice but not cattle [Kennedy et al., Abstracts of the 97th General Meeting of the American Society for Microbiology. B-287:78 (1997)]. Likewise, another strain of S. dublin, SL5631, with a deletion affecting gene aroA was highly protective against lethal challenge to a heterologous challenge strain in mice [Lindberg et al., Infect Immun. 61:1211–1221 (1993)] but not cattle [Smith et al., Am J Vet Res. 54:1249–1255 (1993)].

Third, genetically engineered Salmonella strains that contain a mutation in only a single gene may spontaneously mutate and "revert" to the virulent state. The introduction of mutations in two or more genes tends to provide a high level of safety against restoration of pathogenicity by recombination [Tacket et al., Infect Immun. 60:536–541 (1992)]. However, the use of double or multiple gene disruptions is unpredictable in its effect on virulence and immunogenicity; the introduction of multiple mutations may overattenuate a bacteria for a particular host [Linde et al., Vaccine 8:278–282 (1990); Zhang et al., Microb. Pathog., 26(3):121–130 (1999)].

Of interest to the present invention is the identification of pathogenicity islands (PAIs) in Salmonella and other bacteria, which are large, sometimes unstable, chromosomal regions harboring clusters of genes that often define virulence characteristics in enteric bacteria. The DNA base composition of PAIs often differs from those of the bacterial chromosomes in which they are located, indicating that they have probably been acquired by horizontal gene transfer. One Salmonella pathogenicity island containing genes required for epithelial cell invasion has been identified at around 63 centisomes (cs) on the S. typhimurium chromosome, and has been shown to contain genes encoding components of a type III (contact-dependent) secretion system, secreted effector proteins, and associated regulatory proteins [Millis et al., Mol Microbiol 15(4):749–59 (1995)] A second Salmonella PAI of 40 kb is located at 30.7 and has been designated Salmonella pathogenicity island 2 (SPI2) [Shea et al., Proc. Nat'l Acad. Sci. USA, 19;93(6):2593–2597 (1996)]. Nucleotide sequence analysis of regions of SPI2 revealed genes encoding a second type III secretion apparatus that has been suggested to be involved at a stage of pathogenesis subsequent to epithelial cell penetration. Mutations in some genes within SPI2 have been shown to result in attenuation of bacterial virulence in mice. See U.S. Pat. No. 5,876,931; Shea et al., Proc. Natl. Acad. Sci. USA, 93:2593–2597 (1996); Ochman et al., Proc Natl Acad Sci USA, 93(15):7800–7804 (1996); Hensel et al., J.

Bacteriol., 179(4):1105–1111 (1997); Hensel et al., Molec. Microbiol., 24(1):155–167 (1997); Dunyak et al., poster presented at 97th General Meeting of the American Society for Microbiology (1997), p. 76.

A need continues to exist for more safe and efficacious live attenuated Salmonella vaccines that ideally do not need to be administered at very large doses.

BRIEF SUMMARY OF THE INVENTION

The present invention relates to safe and efficacious vaccines employing one or more strains of attenuated mutant gram-negative bacteria in which one or more genes homologous to genes within Salmonella pathogenicity island 2 (SPI2) have been inactivated, preferably by deletion of about 5% to about 100% of the gene, most preferably by deletion of about 50% or more of the gene. Specifically contemplated are vaccines comprising one or more species of attenuated mutant Salmonella bacteria in which one or more genes, and preferably two or more genes, within SPI2 have been inactivated. In a preferred embodiment, one or more of the ssa genes, particularly ssaT ssaJ, ssaC or ssaM genes, have been inactivated in the mutant bacteria. The invention is based on results of extensive safety and efficacy testing of these vaccines, including vaccines containing more than one serotype of Salmonella, in animal species other than rodents, including cattle and pigs.

According to one aspect of the present invention, vaccine compositions are provided that comprise an immunologically protective amount, of a first attenuated mutant Salmonella bacterium in which one or more ssa genes are inactivated. In one embodiment, the ssa genes are selected from the group consisting of ssaT, ssaJ, ssaC and ssaM. Suitable amounts will vary but may include about $10^9$ bacteria or less. In these mutant bacteria, the inactivated gene(s) is/are preferably inactivated by deletion of a portion of the coding region of the gene. Alternatively, inactivation is effected by insertional mutation. Any species of Salmonella bacteria, particularly S. enterica subspecies and subtypes, may be mutated according to the invention, including Salmonella from serogroups A, B, $C_1$, $C_2$, D, and $E_1$. All of the Salmonella serovars belong to two species: S. bongori and S. enterica. The six subspecies of S. enterica are: S. enterica subsp. enterica (I or 1), S. enterica subsp. salamae (II or 2), S. enterica subsp. arizonae (IIIa or 3a), S. enterica subsp. diarizonae (IIIb or 3b), S. enterica subsp. houtenae (IV or 4), S. enterica subsp. indica (VI or 6). Exemplary subspecies include: S. Choleraesuis, S. Typhimurium, S. Typhi, S. Paratyphi, S. Dublin, S. Enteritidis, S. Gallinarum, S. Pullorum, Salmonella Anatum, Salmonella Hadar, Salmonella Hamburg, Salmonella Kentucky, Salmonella Miami, Salmonella Montevideo, Salmonella Ohio, Salmonella Sendai, Salmonella Typhisuis.

Two or more virulence genes may be inactivated in the mutant Salmonella bacteria, of which at least one gene is a gene within SPI2. In one aspect, the gene is an ssa gene. Preferably, two genes selected from the group consisting of ssaT, ssaJ and ssaC have been inactivated. Most preferably, the combination of ssaT and ssaC, or ssaT and ssaJ have been inactivated.

The vaccine composition may further comprise a second attenuated mutant Salmonella bacterium in which one or more ssa genes have been inactivated. In one aspect, the ssa gene is selected from the group consisting of ssaT, ssaJ and ssaC. Preferably, the first and second mutant Salmonella bacteria are of different serotypes. For cattle, vaccines comprising both S. dublin and S. typhimurium are preferred.

The invention also provides methods of immunizing, i.e., conferring protective immunity on, an animal by administering the vaccine compositions of the invention. Signs of protective immunity are described below. The invention further provides methods of reducing transmission of infection by administering vaccines of the invention in amounts effective to reduce amount or duration of bacterial shedding during infection. Animals that are suitable recipients of such vaccines include but are not limited to cattle, sheep, horses, pigs, poultry and other birds, cats, dogs, and humans. Methods of the invention utilize any of the vaccine compositions of the invention, and preferably, the vaccine comprises an effective amount of an attenuated, non-reverting mutant *Salmonella* bacterium in which one or more genes within the SPI2 region have been inactivated, either by deleting a portion of the gene(s), or, alternatively, by insertional mutation. In one aspect, methods utilize attenuated bacteria wherein an ssa gene is inactivated, and preferably the ssa gene is selected from the group consisting of ssaT, ssaJ, ssaC, and ssaM.

According to another aspect of the invention, the attenuated mutant *Salmonella* bacterium may further comprise a polynucleotide encoding a non-*Salmonella* polypeptide. Administration of the mutant bacteria or a vaccine composition comprising the mutant bacteria thus provides a method of delivering an immunogenic polypeptide antigen to an animal.

Numerous additional aspects and advantages of the invention will become apparent to those skilled in the art upon consideration of the following detailed description of the invention which describes presently preferred embodiments thereof.

DETAILED DESCRIPTION OF THE INVENTION

The present invention provides vaccines, or immunogenic compositions, comprising one or more species of attenuated mutant *Salmonella* bacteria in which one or more virulence genes, preferably genes within SPI2, have been deleted. An advantage of the vaccines of the present invention is that the live attenuated mutant bacteria can be administered as vaccines at reasonable doses, via a variety of different routes, and still induce protective immunity in the vaccinated animals. Another advantage is that mutant bacteria containing inactivations in two different genes are non-reverting, or at least are much less likely to revert to a virulent state.

Risk of reversion can be assessed by passaging the bacteria multiple times (e.g., 5 passages) and administering the resulting bacteria to animals. Non-reverting mutants will continue to be attenuated.

The examples herein demonstrate that inactivation of two or more genes within SPI2 does not further attenuate (or overattenuate) the bacteria compared to bacteria in which only a single gene has been inactivated. The examples also demonstrate that deletion of genes within SPI2 result in safe, efficacious vaccines as shown by observable reductions in adverse signs and symptoms associated with infection by wild type bacteria. The exemplary vaccines of the present invention have been shown to confer superior protective immunity compared to other vaccines containing live attenuated bacteria, e.g., Salmo Shield®TD (Grand Laboratories, Inc.) and mutant *Salmonella* bacteria containing Δrfa K or Δcya Δcrp mutations. The examples further demonstrate that a combination vaccine containing two or more strains of attenuated mutant *Salmonella* of different serotypes is efficacious and that inclusion of the different serotypes does not cause interference with the immune response.

Figure 4:
FIG. 4 shows the organization of SPI2 in *S. typhimurium*, which was assembled using sequences available on GenBank (Accession #'s AJ224892, Z95891, U51927, Y09357 and X99944). Predicted open reading frames are shown as open boxes with the orientation of the open reading frame indicated. The diagram is drawn to scale. Indicated at the bottom are the locations of ssaC, ssaJ and ssaT deletions.

When two or more genes within SPI2 are inactivated, the two genes may be from the same or different SPI2 "regions" (e.g., the export machinery, effector proteins, and sensor/regulator regions). The genes may also be from the same or different functional groups as illustrated in FIG. 4, which include the structural components, ssa (secretion system apparatus, e.g., ssaB, ssaC, ssaD, ssaE, ssaF, ssaG, ssaH, ssaI, ssaJ, ssaK, ssaL, ssaM, ssaN, ssaO, ssaP, ssaQ, ssaR, ssaS, ssaT, and/or ssaU) secreted targets of the type III secretion system, sse (secretion system effector), the two-component sensor regulator system, ssr (secretion system regulator), and the chaperones for the secreted proteins, ssc (secretion system chaperone).

The nucleotide sequence of ssaT from *S. dublin* is set forth in SEQ ID NO: 1. The nucleotide sequence of ssaT from *S. typhimurium* is set forth in SEQ ID NO: 2. As used herein, "ssaT" includes SEQ ID NOS: 1, 2 and other *Salmonella* species equivalents thereof, e.g., full length *Salmonella* nucleotide sequences that hybridize to the non coding complement of SEQ ID NO: 1 or 2 under stringent conditions, wherein stringent conditions comprise hybridization in 50% formamide with washing at 650° C. (e.g., as described in FIG. 4 of Shea et al., Proc. Nat'l. Acad. Sci. USA, 93:2593–2597 (1996), incorporated herein by reference), and full length *Salmonella* nucleotide sequences that have 90% sequence identity to SEQ ID NO: 1 or 2. *Salmonella* species equivalents can be easily identified by those of ordinary skill in the art and also include nucleotide sequences with, e.g. 90%, 95%, 98% and 99% identity to SEQ ID NO: 1 or 2.

The nucleotide sequence of ssaJ from *S. dublin* is set forth in SEQ ID NO: 3. The nucleotide sequence of ssaJ from *S. typhimurium* is set forth in NO: 4. As used herein, "ssaJ" includes SEQ ID NOS: 3, 4, and other *Salmonella* species equivalents thereof, e.g., full length *Salmonella* nucleotide sequences that hybridize to the non coding complement of SEQ ID NO: 3 or 4 under stringent conditions, and full length *Salmonella* nucleotide sequences that have 90% sequence identity to SEQ ID NO: 3 or 4. *Salmonella* species equivalents can be easily identified by those of ordinary skill in the art and also include nucleotide sequences with, e.g., 90%, 95%, 98% and 99% identity to SEQ ID NO: 3 or 4.

The nucleotide sequence of ssaC from *S. dublin* is set forth in SEQ ID NO: 5. The nucleotide sequence of ssaC from *S. typhimurium* is set forth in SEQ ID NO: 6. As used herein, "ssaC" includes SEQ ID NOS: 5, 6, and other *Salmonella* species equivalents thereof, e.g., full length Salmonella nucleotide sequences that hybridize to the non coding complement of SEQ ID NO: 5 or 6 under stringent conditions, and full length Salmonella nucleotide sequences that have 90% sequence identity to SEQ ID NO: 5 or 6. Salmonella species equivalents can be easily identified by those of ordinary skill in the art and also include nucleotide sequences with, e.g., 90%, 95%, 98% and 99% identity to SEQ ID NO: 5 or 6.

The nucleotide sequence of ssaM from *S. dublin* is set forth in SEQ ID NO: 30. The nucleotide sequence of ssaM from *S. typhimurium* is set forth in SEQ ID NO: 7. As used herein, "ssaM" includes SEQ ID NOS: 7, 30 and other Salmonella species equivalents thereof, e.g., full length *Salmonella* nucleotide sequences that hybridize to the non coding complement of SEQ ID NO: 7 or 30 under stringent conditions, and full length *Salmonella* nucleotide sequences that have 90% sequence identity to SEQ ID NO: 7 or 30. *Salmonella* species equivalents can be easily identified by those of ordinary skill in the art and also include nucleotide sequences with, e.g., 90%, 95%, 98% and 99% identity to SEQ ID NO: 7 or 30.

The invention also contemplates that equivalent genes (e.g., greater than 80% homology) in other gram negative bacteria can be similarly inactivated to provide efficacious vaccines.

The nucleotide sequences of other genes in SPI2 can be assembled using sequences available on GenBank (e.g., Accession #'s AJ224892, Z95891, U51927, Y09357 and X99944) which cover SPI2.

As used herein, an "inactivated" gene means that the gene has been mutated by insertion, deletion or substitution of nucleotide sequence such that the mutation inhibits or abolishes expression and/or biological activity of the encoded gene product. The mutation may act through affecting transcription or translation of the gene or its mRNA, or the mutation may affect the polypeptide gene product itself in such a way as to render it inactive.

In preferred embodiments, inactivation is carried by deletion of a portion of the coding region of the gene, because a deletion mutation reduces the risk that the mutant will revert to a virulent state. For example, some, most (e.g., half or more) or virtually all of the coding region may be deleted (e.g., about 5% to about 100% of the gene, but preferably about 20% or more of the gene, and most preferably about 50% or more of the gene may be deleted). Alternatively, the mutation may be an insertion or deletion of even a single nucleotide that causes a frame shift in the open reading frame, which in turn may cause premature termination of the encoded polypeptide or expression of an completely inactive polypeptide. Mutations can also be generated through insertion of foreign gene sequences, e.g., the insertion of a gene encoding antibiotic resistance.

Deletion mutants can be constructed using any of a number of techniques well known and routinely practiced in the art. In one example, a strategy using counterselectable markers can be employed which has commonly been utilized to delete genes in many bacteria. For a review, see, for example, Reyrat, et al., *Infection and Immunity* 66:4011–4017 (1998), incorporated herein by reference. In this technique, a double selection strategy is often employed wherein a plasmid is constructed encoding both a selectable and counterselectable marker, with flanking DNA sequences derived from both sides of the desired deletion. The selectable marker is used to select for bacteria in which the plasmid has integrated into the genome in the appropriate location and manner. The counterselecteable marker is used to select for the very small percentage of bacteria that have spontaneously eliminated the integrated plasmid. A fraction of these bacteria will then contain only the desired deletion with no other foreign DNA present. The key to the use of this technique is the availability of a suitable counterselectable marker.

In another technique, the cre-lox system is used for site specific recombination of DNA. The system consists of 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, it is possible to delete the targeted gene of interest in the *Salmonella* genome and to replace it with a selectable marker (e.g., a gene coding for kanamycin resistance) that is flanked by the lox sites. Transient expression (by electroporation of a suicide plasmid containing the cre gene under control of a promoter that functions in *Salmonella* of the cre recombinase should result in efficient elimination of the lox flanked marker. This process would result in a mutant containing the desired deletion mutation and one copy of the lox sequences.

In another approach, it is possible to directly replace a desired deleted sequence in the *Salmonella* genome with a marker gene, such as green fluorescent protein (GFP), β-galactosidase, or luciferase. In this technique, DNA segments flanking a desired deletion are prepared by PCR and cloned into a suicide (non-replicating) vector for *Salmonella*. An expression cassette, containing a promoter active in *Salmonella* and the appropriate marker gene, is cloned between the flanking sequences. The plasmid is introduced into wild-type *Salmonella*. Bacteria that incorporate and express the marker gene (probably at a very low frequency) are isolated and examined for the appropriate recombination event (i.e., replacement of the wild type gene with the marker gene).

In order for a modified strain to be effective in a vaccine formulation, the attenuation must be significant enough to prevent the pathogen from evoking severe clinical symptoms, but also insignificant enough to allow limited replication and growth of the bacteria in the recipient. The recipient is a subject needing protection from a disease caused by a virulent form of *Salmonella* or other pathogenic microorganisms. The subject to be immunized may be a human or other mammal or animal, for example, farm animals including cows, sheep, pigs, horses, goats and poultry (e.g., chickens, turkeys, ducks and geese) and companion animals such as dogs and cats; exotic and/or zoo animals. Immunization of both rodents and non-rodent animals is contemplated.

An "immunologically protective amount" of the attenuated mutant bacteria is an amount effective to induce an immunogenic response in the recipient that is adequate to prevent or ameliorate signs or symptoms of disease, including adverse health effects or complications thereof, caused by infection with wild type *Salmonella* bacteria. Either humoral immunity or cell-mediated immunity or both may be induced. The immunogenic response of an animal to a vaccine composition may be evaluated, e.g., indirectly through measurement of antibody titers, lymphocyte proliferation assays, or directly through monitoring signs and symptoms after challenge with wild type strain.

The protective immunity conferred by a vaccine can be evaluated by measuring, e.g., reduction in clinical signs such as mortality, morbidity, temperature number and % of days of diarrhea, milk production or yield, average daily weight gain, physical condition and overall health and performance of the subject.

When a combination of two or more different serotypes of bacteria are administered, it is highly desirable that there be little or no interference among the serotypes such that the host is not prevented from developing a protective immune response to one of the two or more serotypes administered. Interference can arise, e.g., if one strain predominates in the host to the point that it prevents or limits the host from developing a protective immune response to the other strain. Alternatively, one strain may directly inhibit the other strain.

In addition to immunizing the recipient, the vaccines of the invention may also promote growth of the recipient and/or boost the recipient's immunity and/or improve the recipient's overall health status. Components of the vaccines of the invention, or microbial products, may act as immunomodulators that may inhibit or enhance aspects of the immune system. For example, the vaccines of the invention may signal pathways that would recruit cytokines that would have an overall positive benefit to the host.

The vaccines of the present invention also provide veterinary and human community health benefit by reducing the shedding of virulent bacteria by infected animals. Either bacterial load being shed (the amount of bacteria, e.g., CFU/ml feces) or the duration of shedding (e.g., number of % of days shedding is observed) may be reduced, or both. Preferably, shedding load is reduced by about 10% or more compared to unvaccinated animals preferably by 20% or more, and/or shedding duration is reduced by at least 1 day, or more preferably 2 or 3 days, or by 10% or more or 20% or more.

While it is possible for an attenuated bacteria of the invention to be administered alone, one or more of such mutant bacteria are preferably administered in conjunction with suitable pharmaceutically acceptable excipient(s), diluent(s), adjuvant(s) or carrier(s). The carrier(s) must be "acceptable" in the sense of being compatible with the attenuated mutant bacteria of the invention and not deleterious to the subject to be immunized. Typically, the carriers will be water or saline which will be sterile and pyrogen free.

Any adjuvant known in the art may be used in the vaccine composition, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachis oil), liposomes, Pluronic® polyols, the Ribi adjuvant system (see, for example GB-A-2 189 141), or interleukins, particularly those that stimulate cell mediated immunity. An alternative adjuvant consisting of extracts of Amycolata, a bacterial genus in the order Actinomycetales, has been described in U.S. Pat. No. 4,877,612. Additionally, proprietary adjuvant mixtures are commercially available. The adjuvant used will depend, in part, on the recipient organism. The amount of adjuvant to administer will depend on the type and size of animal. Optimal dosages may be readily determined by routine methods.

The vaccine compositions optionally may include vaccine-compatible pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The vaccine compositions can be packaged in forms convenient for delivery. The compositions can be enclosed within a capsule, caplet, sachet, cachet, gelatin, paper, or other container. These delivery forms are preferred when compatible with entry of the immunogenic composition into the recipient organism and, particularly, when the immunogenic composition is being delivered in unit dose form. The dosage units can be packaged, e.g., in tablets, capsules, suppositories or cachets.

The vaccine compositions may be introduced into the subject to be immunized by any conventional method including, e.g., by intravenous, intradermal, intramuscular, intramammary, intraperitoneal, or subcutaneous injection; by oral, transdermal, sublingual, intranasal, anal, or vaginal, delivery. The treatment may consist of a single dose or a plurality of doses over a period of time.

Depending on the route of administration, suitable amounts of the mutant bacteria to be administered include $\sim10^9$ bacteria or less, provided that an adequate immunogenic response is induced by the vaccinee. Doses of $\sim10^{10}$ or less or $\sim10^{11}$ or less may be required to achieve the desired response. Doses significantly higher than $\sim10^{11}$ may not be commercially desirable.

Another aspect of the invention involves the construction of attenuated mutant bacteria that additionally comprise a polynucleotide sequence encoding a heterologous polypeptide. For example, for Salmonella, a "heterologous" polypeptide would be a non-*Salmonella* polypeptide not normally expressed by *Salmonella* bacteria. Such attenuated mutant bacteria can be used in methods for delivering the heterologous polypeptide or DNA. For example, *Salmonella* could be engineered to lyse upon entry into the cytoplasm of a eukaryotic host cell without causing significant damage, thereby becoming a vector for the introduction of plasmid DNA into the cell. Suitable heterologous polypeptides include immunogenic antigens from other infectious agents (including gram-negative bacteria, gram-positive bacteria and viruses) that induce a protective immune response in the recipients, and expression of the polypeptide antigen by the mutant bacteria in the vaccine causes the recipient to be immunized against the antigen. Other heterologous polypeptides that can be introduced using the mutant *Salmonella* include immunomodulatory molecules e.g., cytokines or "performance" proteins such as growth hormone, GRH, and GDF-8.

Example 1 addresses the construction of attenuated mutant *Salmonella* bacteria containing defined single or double deletions in the ssaT, ssaJ, ssaC, rfaK and glnA genes; and construction of mutant *Salmonella* containing inactivating insertions. Example 2 addresses the results of safety and efficacy testing of animals inoculated with these attenuated mutant *Salmonella* bacteria.

EXAMPLE 1

Construction of *Salmonella* Mutants Containing Single and Double Deletions of Selected Genes: ssaT, ssaJ, ssaC, rfaK and glnA A. Construction of pCVD442::Δgene Plasmids.

For each of the *S. typhimurium* and *S. dublin* ssaT, ssaJ, ssaC, rfaK and glnA genes, positive selection suicide vectors based on the plasmid pCVD442 [Donnenberg and Kaper, Infect Immun 59:4310–17 (1991)] were constructed that contained a portion of the 5' and 3' chromosomal regions flanking each gene but with substantial internal deletions (typically >95%) within the gene itself. Gene splicing by overlap extension ("gene SOEing" [Horton et al., Biotechniques 8:528–535 (1990)]) was used to generate DNA fragments which were complementary to the gene to be deleted, but which lacked the majority of the internal nucleotide sequence. The plasmids containing these internally deleted genes were designated pCVD442::ΔssaT, pCVD442::ΔssaJ, pCVD442::ΔssaC, pCVD442::ΔrfaK, and pCVD442::ΔglnA, respectively. These vectors were then used to generate S. typhimurium and S. dublin deletion mutants by allelic exchange. Plasmids containing the S. dublin deleted genes was used to produce the deletions in S. dublin, and plasmids containing the S. typhimirium sequences was used to produce the deletions in S. typhimurium (see Example 1B below).

In brief, two sets of PCR primers were designed to synthesize approximately 600 bp fragments that are complementary to the DNA flanking the 5' and 3' sides of the desired gene. Primers A and D (Table 1) contain chromosomal sequence upstream and downstream, respectively, of the desired gene and each also contains the nucleotide sequence for a desired restriction endonuclease site. Primer B spans the upstream junction between the sequences immediately flanking the 5' side of the gene and the gene itself and includes some a portion of the 5' end of the gene (in some cases, only the stop codon). Similarly, primer C spans the downstream junction between the sequences immediately flanking the 3' side of the gene and the gene itself, and includes a portion of the 3' end of the gene (in some cases, only the start codon). PCR reactions with S. typhimurium or S. dublin genomic DNA and either primers A and B or primers C and D were performed, yielding PCR products (designated fragments AB and CD, respectively) of approximately 600 bp with sequences corresponding to the upstream or downstream flanking regions of the desired gene, respectively. Each AB or CD fragment also contained the desired restriction site (Xba I for ssaT, ssaJ, ssaC, and glnA and Sal I for rfaK). A second PCR reaction using fragments AB and CD with primers A and D was then performed, yielding a PCR product designated fragment AD. Fragment AD is complementary to the nucleotide sequence surrounding the targeted gene, but contains essentially a complete deletion of the targeted sequences (>95% deletion) for ssaS, ssaT, rfaK, and glnA, and a deletion of the C-terminal half (~50% deletion) for ssaJ (see FIGS. 1–3). The resulting PCR product for each of the S. dublin or S. typhimurium ΔssaT, ΔssaJ, ΔssaC, ΔrfaK, and ΔglnA genes was then cloned through various vectors and host strains and finally inserted into the multiple cloning site of vector pCVD442 in host strain SM10λpir.

Figure 1:
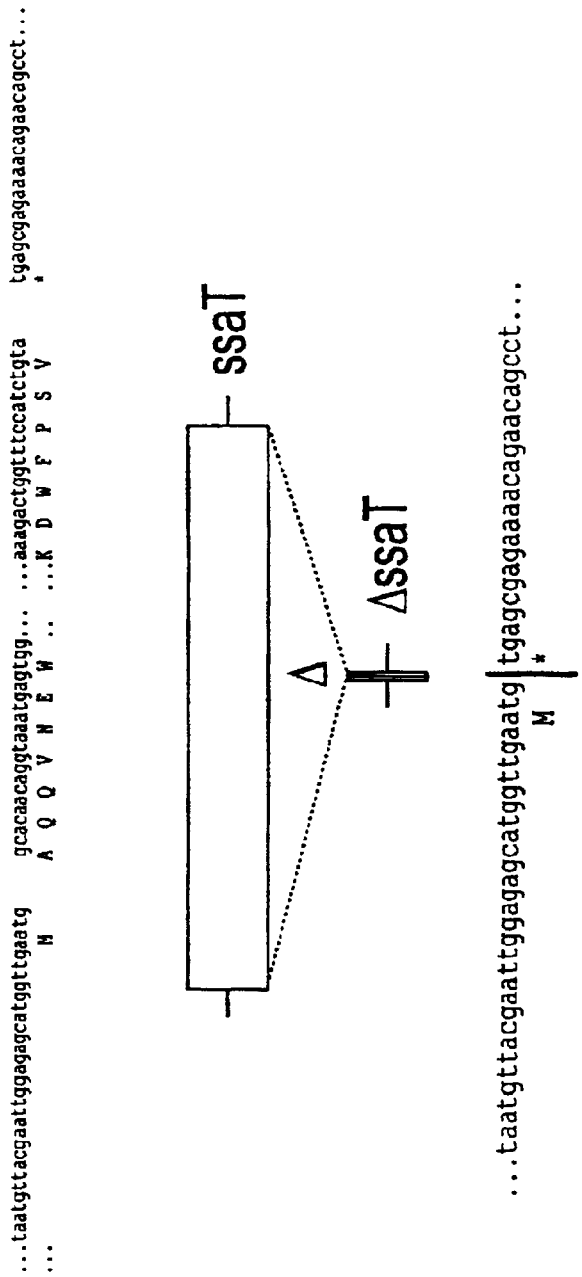
FIGS. 1, 2 and 3 show a schematic representation of the *S. typhimurium* nucleotide sequences flanking the internal deletions of the ssaT, ssaJ and ssaC genes, respectively, in the wild type and the mutant genome. The top sequence shows the nucleotides flanking the deletion points, while the lower sequence shows the DNA sequence present in the deleted locus. Small letters indicate nucleotides and capital letters specify amino acids.
Figure 2:
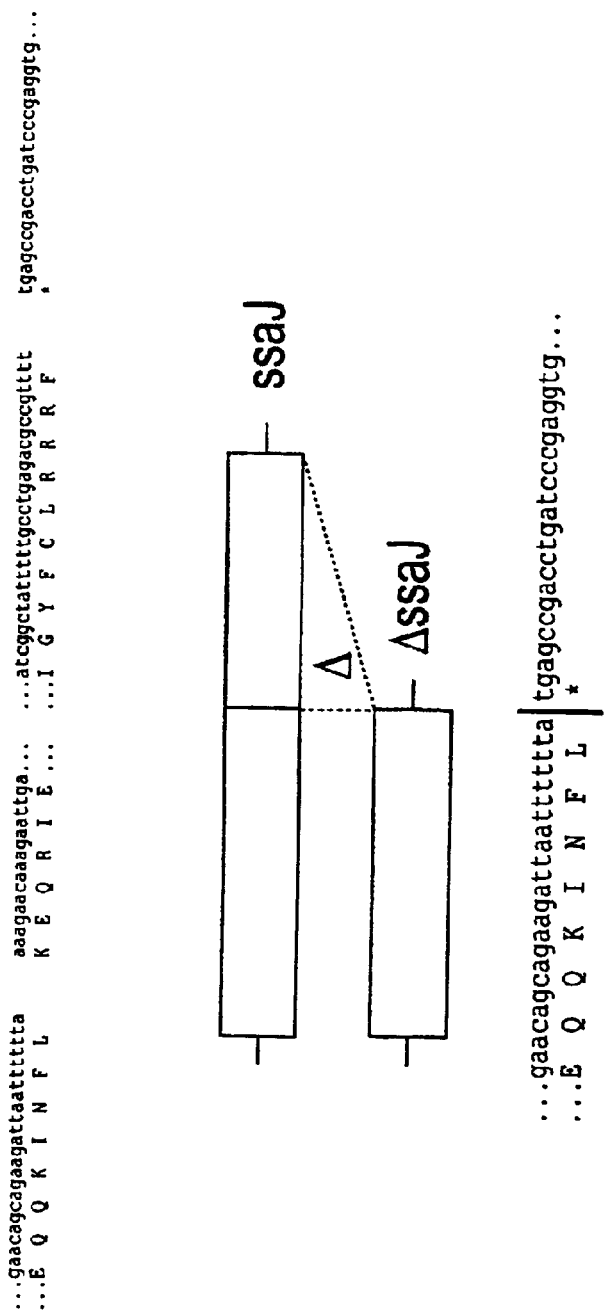
Figure 3:
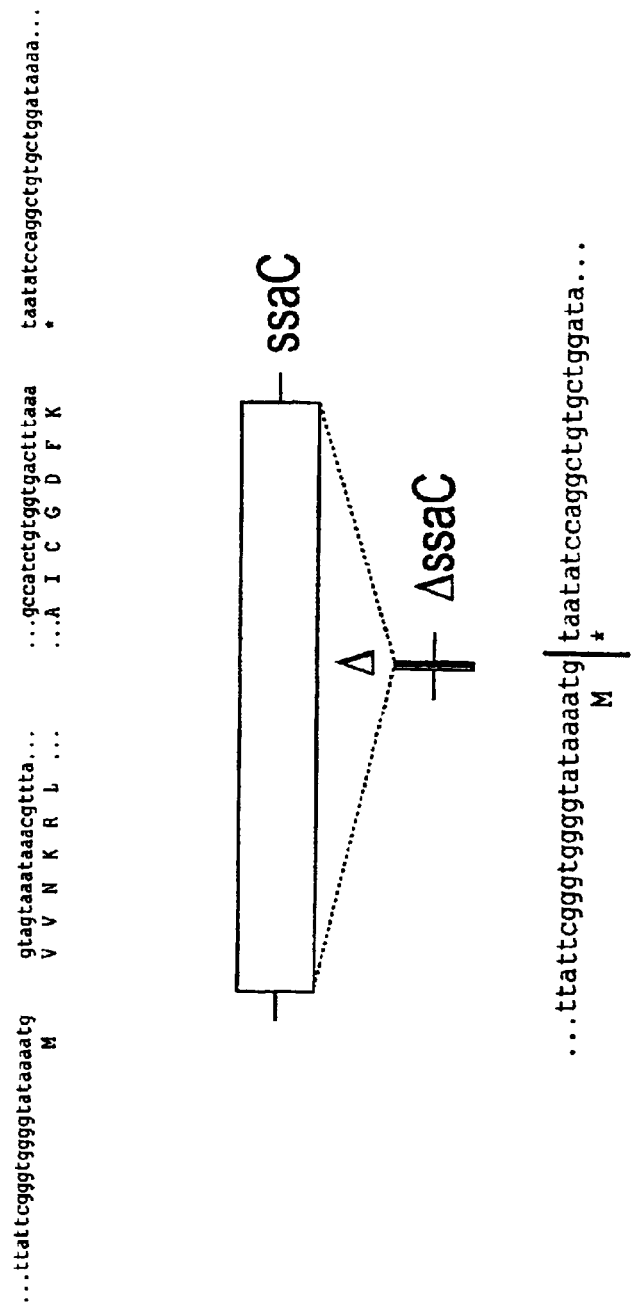

FIGS. 1, 2 and 3 show the nucleotide sequences flanking the junctions of the ssaT, ssaJ and ssaC genes in the wild type and the mutant genome. These deletions were engineered to remove as much of the open reading frame as feasible. In the case of the ssaC (1052 bp) and ssaT (779 bp) genes the entire open reading frame of each was deleted, leaving only the start and stop codons (6 bp) after the deletion was generated. Only the C-terminal half of the ssaJ gene could be removed when the deletion was created. This reduced the size of the gene from 749 bp to 324 bp.

FIG. 4 shows the genetic arrangement of the SPI2 locus in S. typhimurium. This is a compilation of the SPI2 region of S. typhimurium assembled using sequences available on GenBank (Accession #'s AJ224892, Z95891, U51927, Y09357 and X99944). Also shown are the positions of the deletions constructed in the ssa C, ssaJ and ssaT genes.

TABLE 1

Primers used in construction of modified S. typhimurium and dublin genes*.

| Gene | Primer Number (Letter) | Sequence ID NOs: | Primer Sequence | Restriction Site |
|---|---|---|---|---|
| ssaT | 642 (A) | 10 | 5'-GCCAATCTAGAAATTATTTTCGGAATTTGATAAA-3' | XbaI |
| | 643 (B) | 11 | 5'-AGGCTGTTCTGTTTTCTCGCTCACATTCAACCATGCTCTCCAATTCGTA-3' | — |
| | 644 (C) | 12 | 5'-TACGAATTGGAGAGCATGGTTGAATGTGAGCGAGAAAACAGAACAGCCT-3' | — |
| | 645 (D) | 13 | 5'-GCCAATCTAGATCTTTTCTAATCTTATAATATTG-3' | XbaI |
| ssaJ | 638 (A) | 14 | 5'-GCCAATCTAGACTGCAGAACCGAGCCAGGAGCAA-3 | XbaI |
| | 639 (B) | 15 | 5'-CACCTCGGGATCAGGTCGGCTCATAAAAAATTAATCTTCTGCTGTT-3' | — |
| | 640 (C) | 16 | 5'-AACAGCAGAAGATTAATTTTTTATGAGCCGACCTGATCCCGAGGTG-3' | — |
| | 646 (D) | 17 | 5'-GCCAATCTAGAGAAGATAATCTCGGTAAGAGAAGT-3' | XbaI |
| ssaC | 634 (A) | 18 | 5'-GCCAATCTAGATTCAAATTGTAAGTTTTTATGTCAAT-3' | XbaI |
| | 635 (B) | 19 | 5'-TTTATCCAGCACAGCCTGGATATTACATTTTATACCCCACCCGAATAAAG-3' | — |
| | 647 (C) | 20 | 5'-TTATTCGGGTGGGGTATAAAATGTAATATCCAGGCTGTGCTG-3' | — |
| | 637 (D) | 21 | 5'-GCCAATCTAGATTCCCGGCATCAACAAATAAACT-3' | XbaI |
| rfaK | 882 (A) | 22 | 5'-GCCAAGTCGACATAGTAGGTGTTCTGTGGGCAATA-3' | SalI |

TABLE 1-continued

Primers used in construction of modified S. typhimurium and dublin genes*.

| Gene | Primer Number (Letter) | Sequence ID NOs: | Primer Sequence | Restriction Site |
|---|---|---|---|---|
| | 883 (B) | 23 | 5'-TTCTGGATTATAGCTATTATGATTGTTTGATAAGTGATTGAGTCCTGA-3' | — |
| | 884 (C) | 24 | 5'-TCAGGACTCAATCACTTATCAAACAATCATAATAGCTATAATCCAGAA-3' | — |
| | 885 (D) | 25 | 5'-GCCAAGTCGACGTGTACGAACAGGCTTCAGTGGAT-3' | SalI |
| glnA | 886 (A) | 26 | 5'-GCCAATCTAGATCAGGCATTAGAAATAGCGCGTTA-3' | XbaI |
| | 887 (B) | 27 | 5'-ATTTTTAATATACGATTAAACGCTCAAACATTTTGCCTTCTTCAAAGA-3' | — |
| | 888 (C) | 28 | 5'-TCTTTGAAGAAGGCAAAATGTTTGAGCGTTTAATCGTATATTAAAAAT-3' | — |
| | 889 (D) | 29 | 5'-GCCAATCTAGATGCTCCTGACTCAGACGACGCTGG-3' | XbaI |

*PCR primers used in generating the left (5') and right (3') flanking regions of the ssaT, ssaJ, ssaC, rfaK and glnA genes. Primers A/B and C/D are the 5' and 3' primer sets, respectively, for that gene. Primers A and D are the primers that are the furthest upstream and downstream from that gene and were designed to incorporate the restriction sites indicated into the PCR product.

The S. dublin and S. typhimurium genes are similar enough that the same primers could be used for both serotypes.

B. Construction of Deletion Mutants of S. typhimurium and S. dublin

The pCVD442::Δgene plasmids constructed in Example 1 A above were used to produce deletion mutants by homologous recombination with the appropriate Salmonella strain i.e., a plasmid containing the S. dublin deleted gene was used to produce the deletion in S. dublin, and a plasmid containing the S. typhimirium sequences was used to produce the deletion in S. typhimurium. The plasmid pCVD442 is a positive selection suicide vector. It contains the origin of replication for R6K plasmids (ori), the mobilization gene for RP4 plasmids (mob), the gene for ampicillin resistance (bla), the sacB gene from B. subtilis, which encodes the gene for levan sucrase and a multiple cloning site.

The plasmid pCVD442 can be maintained extrachromosomally only in bacterial strains producing the X protein, the pir gene product (e.g. E. coli SM10λpir or DH5αλpir). Introduction of a pCVD442 based vector into a nonpermissive host strain (S. typhimurium or S. dublin), by conjugation and selection on Ap (ampicillin) and Nal (nalidixic acid) containing medium, allows the isolation of $Ap^R$ merodiploid isolates in which the plasmid has integrated into the genome of the target strain by homologous recombination with the wild type gene.

In brief, E. coli strain SM10λpir (thi thr leu tonA lacY supE recA::RP4-2-Tc::Mu km )[(Donnenberg and Kaper, Infect Immun 59:4310–17 (1991)] carrying the pCVD442 plasmids with the S. typhimurium or S. dublin ΔssaT, ΔssaJ, ΔssaC, ΔrfaK or ΔglnA genes (designated SM10λpir/pCVD442::Δgene) were mated with $Nal^R$ S. typhimurium MK315N or S. dublin B94-058N, and recombinants were selected on Ap and Nal. Both MK315N and B94-058N are spontaneous $Nal^R$ strains prepared by plating the respective parent strains on LB agar containing 50 μg/ml Nal (clinical isolates from a bovine and a human subject, respectively). The $Ap^R$ $Nal^R$ recombinants recovered must have the plasmid integrated into the chromosome because the plasmid cannot be maintained extrachromosomally. This results in the formation of a merodiploid strain that contains the pCVD442::Δgene plasmid integrated into that gene locus on the chromosome.

The $Ap^R$ $Nal^R$ S. typhimurium MK315N::pCVD442::Δgene and S. dublin B94-058N::pCVD442::Δgene recombinants were then grown under non-selective conditions followed by growth on LA (−sucrose) and TYES (+sucrose) agar. In the absence of selection pressure a spontaneous recombination event can occur in which the pCVD442 plasmid and either the wild-type gene or the deleted gene are excised from the chromosome. Cells retaining the pCVD442 plasmid were counterselected on TYES agar by the toxic products produced from the breakdown of sucrose by levan sucrase, encoded by the sacB gene. Consequently, the number of colonies on TYES agar is significantly reduced relative to the number on LA. After confirming the $Ap^S$ phenotype of the isolated colonies on the TYES agar, the recombinants were analyzed by PCR to determine whether the wild-type gene or the deleted gene had been retained.

In initial experiments, the donor and recipient were mated for 5 hrs. on LB agar and then selected on LB agar containing Nal (20 or 100 μg/ml) and Ap (20 or 100 μg/ml). While heavy growth appeared on the initial selection plate few, if any, of the isolated colonies could be confirmed as $Ap^R$ $Nal^R$. The inability to isolate recombinant growth was likely due to the growth of the recipient as a result of the degradation of ampicillin by the release of β-lactamase from the donor cells. To overcome this problem, mating and selection conditions were designed that favored the recombinants and selected against the donor and recipient strains. Specifically, recipient and donor strains were mated overnight on LB agar or modified M9 agar (Difco Laboratory, Detriot, Mich.), followed by enrichment of recombinants by growth in selective (Nal and Ap (75 μg/ml)) LB broth (Difco Laboratory, Detriot, Mich.), and isolation on selective (Nal and Ap (75 μg/ml)) agar medium. Mating on modified M9 agar allowed conjugation to occur, but limited replication, which reduced the number of donor and recipient cells introduced to the selection broth. Growth to early logarithmic phase in selection broth favored the replication of the recombinants but not the donor and recipient strains. Subsequent selection on LB agar Nal Ap (75 μg/ml each) further favored the recombinants over the donor and recipient, which was confirmed when almost all isolated colonies were $Ap^R$ $Nal^R$. This procedure yielded merodiploid S. typhimurium or S. dublin recombinants carrying the appropriate plasmid pCVD442::Δgene inserted into the genome.

Meridiploid isolates were then grown under non-selective conditions to late logarithmic phase and inoculated to LB agar and TYES agar. During non-selective growth a spontaneous recombination event can occur between the duplicated sequences in the merodiploid state, leaving a copy of either the wild type or deleted gene in the chromosome. Growth on sucrose (TYES) selects against those cells which have not undergone the second recombination event because the products of levan sucrase, encoded by the sacb gene on the pCVD442 plasmid, are toxic to gram-negative cells. Consequently, the number of colonies on TYES agar is much lower than on LA. In our hands, it was critical to incubate the TYES plates at room temperature for the selection to be successful. Incubation at higher temperatures (30° or 37° C.) did not reduce the number of colonies on TYES relative to LA indicating that selection for pCVD442-negative cells did not occur.

TYES-grown colonies were streaked for single colony and the $Nal^R$ $Ap^S$ phenotype confirmed. PCR analysis of the genomic DNA of the colonies using the appropriate Primers A and D described above for each gene was then performed to determine whether the deleted or wild type gene had been retained in the chromosome. For ssaT, a PCR product of 1206 bp (vs. 1980 bp for wild type gene) indicated that the gene had been deleted. For ssaJ, a PCR product of 1074 bp (vs. 1500 bp for wild type gene) indicated that the gene had been deleted. For ssaC, a PCR product of 1229 bp (vs. 2275 bp for wild type gene) indicated that the gene had been deleted. For rfaK, a PCR product of 1300 bp (vs. 2400 bp for wild type gene) indicated that the gene had been deleted. For glnA, a PCR product of 1161 bp (vs. 2411 for wild type gene) indicated that the gene had been deleted.

Although theoretically 50% of these isolates should carry the deleted gene, the actual percentage of isolates carrying the deleted gene was quite variable, ranging from 1.4% (1 out of 73 isolates) for the S. dublin glnA gene to 80% (4 out of 5) for the S. dublin ssaJ gene, suggesting that the excision of the gene was not random. Deletion mutants were confirmed to be S. typhimurium or S. dublin by serological tests.

C. Construction of Double Deletion Mutants of S. typhimurium and S. dublin

Salmonella double deletion mutants were constructed in the same fashion as the Salmonella single deletion mutants using E. coli and Salmonella strains described above. In brief, E. coli SM10λpir donor strains carrying the pCVD442 plasmid with the deleted ssaT gene (Δssa1) from either S. typhimurium or S. dublin were mated with S. dublin B94-058N or S. typhimurium MK315N mutants with either the deleted ssaC or ssaJ gene (ΔssaC and ΔssaJ), and $Ap^R$ exconjugants were selected. Introduction of the plasmid into the nonpermissive Salmonella host and selection of $Ap^R$ colonies allowed the isolation of merodiploid recombinants in which the pCVD442 plasmid was integrated into the genome by homologous recombination with the wild type gene. Subsequent growth of the merodiploid recombinants to late logarithmic phase under non-selective conditions allowed a spontaneous recombination event to occur between the duplicated sequences in the merodiploid genome, leaving a copy of either the wild type or deleted gene in the chromosome. Colonies grown under these non-selective growth conditions were then inoculated into sucrose containing medium, which selected against those cells which have not undergone the second recombination event. Isolated sucrose resistant colonies of S. typhimurium were analyzed by PCR to identify the desired ssaT deletion mutant.

Despite assaying numerous sucrose resistant colonies by PCR, an S. dublin ssaT deletion mutant could not be identified. The putative B94-058N::ΔssaCssaT and B94-058N::ΔssaJΔssaT recombinants were identified by colony hybridization. The E. coli SM10λpir donor strains carrying the pCVD442 plasmid with the deleted ssa T gene (Δssa T) from S. dublin were mated with S. dublin B94-058N mutants with either the deleted ssaC or ssaJ gene (ΔssaC and ΔssaJ) and selected for sucrose resistant colonies as described above. These colonies were then grown on selective (Ap and Nal) media and then lifted onto nitrocellulose (Schleicher & Schuell nitrocellulose BA85; Schleicher and Schuell, Keene, N.H.). The nitrocellulose blot was processed as described in Davis et al., Basic methods in molecular biology, Elsevier, New York (1986) except that the second and third buffers used were 1 M Tris, pH 7.6, and 1.5 M NaCl-0.25 M Tris, pH 7.6, respectively. The bacterial DNA was crosslinked to the nitrocellulose using a Stratagene UV Stratalinker 1800 (Stratagene, La Jolla, Calif.) using the auto crosslink setting (1200 μJ×100). The blot was prehybridized, hybridized, washed and developed according to the Genius system instructions (Boehringer Mannheim Biochemicals, Indianapolis, Ind.), using the manufacturer's instructions. Internal sequences of the ssat gene was used as the probe during the hybridization step. The probe was generated by PCR using DEL-1680 (5'-TGGCTTTTATTCGACCATTGAGCCTTTC-3'(SEQ ID NO: 8)) and DEL-1681 (5'-TTTATCGCTTTCAACCAAATAGTGATG-3' (SEQ ID NO: 9)) as the primers and suspended B94-058N colonial growth as the DNA template. The DNA probe was labeled by incorporating digoxigenin into the abbreviated ssaT gene using the DIG-High Primer kit (Boehringer Mannheim Biochemicals). The colonies which did not yield a positive signal, putative ssaT deletion mutants, were analyzed for the presence of the wild type or deleted ssaT gene by PCR using suspended colonial growth and primers A and D (see Example 1A) for the ssaT gene as described above.

To isolate the desired double deletion mutants it was necessary to analyze recombinants after non-selective growth using either PCR (S. typhimurium recombinants) or colony hybridization followed by PCR (S. dublin recombinants). In theory the excision of the wild type and deleted gene should occur randomly and at an equal frequency resulting in 50% of the recombinants carrying the deleted gene. As shown in Example 1B, however, the percentage of isolates with the deleted gene was quite variable. The frequency in which the deleted ΔssaT gene was recovered in the putative S. typhimurium MK315N::ΔssaJΔssaT, S. typhimurium MK315N::ΔssaCΔssaT, S. dublin B94-058N::ΔssaCΔssaT and S. dublin B94-058N::ΔssaJΔssaT recombinants was 50% (4 out of 8), 12.5% (1 out of 8), 3.8% (8 out of 209) and 8.9% (14 out of 158), respectively.

PCR analysis of the genomic DNA of putative S. typhimurium and S. dublin double deletion mutants (using the appropriate Primers A and D described above) confirmed the presence of both the ssaC and ssaT or ssaJ and ssaT deleted genes. Deletion mutants were confirmed to be S. typhimurium or S. dublin by serological tests. S. typhimurium and S. dublin mutants were shown to agglutinate in Salmonella O Group B and Salmonella O Group $D_1$ antisera (Difco Laboratory, Detriot, Mich.), respectively, as expected.

D. Construction of *S. chloeraesuis* Mutants

*S. chloeraesuis* mutants were constructed using the STM process generally described in U.S. Pat. No. 5,876,931, incorporated herein by reference. Briefly, each insertional mutation produced carries a different DNA signature tag, which allows mutants to be differentiated from each other. The tags comprise 40-bp variable central regions flanked by invariant "arms" of 20-bp which allow the central portions to be co-amplified by PCR. Tagged mutant strains are assembled in microtiter dishes, then combined to form the "inoculum pool" for infection studies. At an appropriate time after inoculation, bacteria are isolated from the animal and pooled to form the "recovered pool." The tags in the recovered pool and the tags in the inoculum pool are separately amplified, labeled, and then used to probe filters arrayed with the different tags representing the mutants in the inoculum. Mutants with attenuated virulence are those with tags that give hybridization signals when probed with tags from the inoculum pool but not when probed with tags from the recovered pool. STM allows a large number of insertional mutant strains to be screened simultaneously in a single animal for loss of virulence. Using this method, insertional mutants of *S. chloeraesuis* containing a mini-tn5 transposon interrupting the particular gene were generated. Portions of the gene surrounding each transposon were sequenced to identify the insertion site by alignment of the sequence with the corresponding sequence of known *S. typhimurium* genes. The mini-tn5 transposon creating the ΔssaM mutation was located between nucleotide positions 126 and 127 in SEQ ID NO: 7, and the mini-tn5 transposon producing the ΔssaJ mutation was located between nucleotide positions 209 and 210 in SEQ ID NO: 4.

E. Characterization of Single and Double SPI2 Mutants

Data showed that certain of the single and double deletion mutants, specifically ΔssaC and ΔssaCΔssaT, are less invasive than the wild-type and other mutants. This may contribute to slightly better efficacy. It may be that mutants, e.g., ΔssaC mutants, that remain associated with intestinal mucosa for longer periods of time yet have a reduced ability to invade host epithelial cells, are better able to elicit strong mucosal immunity.

EXAMPLE 2

Safety and Efficacy of Single and Double Deletion SPI2 Mutants

A. Efficacy of a *S. chloeraesuis* ΔssaC Mutant as a Vaccine in Swine (Trial No. 704-7923-I-MJK-96-008)

The safety and efficacy of a live attenuated *S. chloeraesuis* ΔssaC mutant as a vaccine was determined in swine (3–4 week old pigs). The pigs (8 pigs per group) were vaccinated either orally via the drinking water or intramuscularly (IM), at a dose of about $\sim 1 \times 10^9$ CFUs/pig. For oral vaccination, 10 ml of the lab grown culture of the vaccine (grown generally as described in Example 2.D. below) was diluted 1:4 in ddH$_2$O. 40 ml of this mixture was further diluted by adding 960 ml of sterile ddH$_2$O; 100 ml of this final mixture was given to pigs orally via a waterer (pigs drank approximately 50 ml of water, giving a final vaccine dose of $\sim 2.6 \times 10^8$ per pig). For the IM vaccination, 27 ml of the 1:4 diluted vaccine culture was added to 3 ml of sterile WFI; 2.5 ml of this mixture was administered intramuscularly to each animal giving a final dose of $\sim 3.0 \times 10^8$ per pig. The pigs were monitored daily for temperature, body weight, fecal consistency scores, physical condition, and mortality. Animals were also monitored for shedding of the vaccine and challenge organisms. All animals were necrospied at termination of the trial and tissues were cultured for the challenge organism.

Following vaccination, no adverse clinical signs of disease were observed in animals vaccinated orally or IM with the ΔssaC mutant except for a short-term elevation in temperature. The pigs were then rechallenged with the highly virulent wild type *S. choleraesuis*, which was a field isolate obtained from a case of salmonellosis, at 28 days post-vaccination. Results showed that administration of the ΔssaC mutant by either oral or intramuscular routes was safe and efficacious against experimentally induced salmonellosis. Non-vaccinates exhibited severe pyrexia, which was accompanied by watery diarrhea, anorexia, dehydration, and death. In contrast, animals vaccinated with the ΔssaC vaccine constructs were resistant to infection. In these animals, there was a statistically significant reduction in both the severity and duration of morbidity, mortality, days of inactivity, and shedding of the challenge organism.

B. Efficacy of a *S. chloeraesuis* ΔssaM or *S. chloeraesuis* ΔssaC Mutants as Vaccines in Swine
(704-7923-I-MJK-96-012)

The safety and efficacy of a live attenuated *S. chloeraesuis* ΔssaM or a *S. chloeraesuis* ΔssaC mutant as a vaccine was determined in swine (3–4 week old pigs). Eight pigs were vaccinated orally via the drinking water at a dose of about $\sim 1 \times 10^9$ CFUs/pig. For oral vaccination, a lab grown vaccine culture (grown generally as described in Example 2.D. below) was diluted 1:4 in ddH$_2$O; 40 ml of this mixture was added to 960 ml of sterile ddH$_2$O; and 100 ml of this final mixture was given to pigs via a waterer. The number of CFUs per ml was determined by performing serial 10-fold dilutions of the final formulation, and plating on agar. The dose per pig was then determined by multiplying the number of CFUs/ml by the number of mls of water consumed by the animal (each pig drank approximately 50 ml of water), giving a final vaccine dose of $\sim 1 \times 10^9$ CFUs/pig. Baseline values for body temperatures, fecal consistency, and physical condition for each animal were collected during the four days immediately prior to vaccination, and were compared to post-vaccination values to assess the safety of each vaccine. The pigs were monitored daily for temperature, body weight, fecal consistency scores, physical condition, and mortality. Animals were also monitored for shedding of the vaccine and challenge organisms. All animals were necrospied at termination of the trial and tissues were cultured for the challenge organism.

Following vaccination, no adverse clinical signs of disease were observed in animals vaccinated orally with either SPI2 mutant except for a short-term elevation in temperature. The pigs were then rechallenged with the highly virulent wild type *S. choleraesuis*, which was a field isolate obtained from a case of salmonellosis, at 28 days post-vaccination. Results showed that administration of either SPI2 mutant by oral routes was safe and efficacious against experimentally induced salmonellosis. Non-vaccinates exhibited severe pyrexia, which was accompanied by watery diarrhea, anorexia, dehydration, and death. In contrast, animals vaccinated with the ΔssaC or ΔssaM vaccine constructs were resistant to infection. In these animals, there was a significant reduction in both the severity and duration of morbidity, mortality, days of inactivity, and shedding of the challenge organism.

C. Efficacy of a *S. chloeraesuis* ΔssaJ or a *S. chloeraesuis* ΔssaC Mutant as Vaccines in Swine
704-7923-I-MJK-97-004

The safety and efficacy of a live attenuated *S. chloeraesuis* ΔssaJ or a *S. chloeraesuis* ΔssaC mutant as a vaccine was determined in swine (56 male & female crossbred pigs, 18–24 days of age at vaccination). Baseline temperatures and clinical scores (mortality, morbidity, diarrhea, shedding of bacteria and average daily weight gain) were recorded on Days 1–4. The pigs were vaccinated orally via the drinking water on Day 4 at a dose of about ~$1 \times 10^9$ CFUs/pig as described above in Example 2B. The pigs were monitored daily for clinical symptoms (% mortality, % morbidity, % diarrhea days, % shedding days, and average daily gain, determined as described in Example 2.D. below) for 21 days post-vaccination (Days 5–25), of which Days 22–25 were considered a baseline before challenge with wild type bacteria. The pigs were then challenged with a highly virulent wild type S. choleraesuis, which was a field isolate obtained from a case of salmonellosis, orally via feed (following a 24 hour fast) at 21 days post-vaccination (Day 25). The pigs continued to be monitored for clinical symptoms for a further 21 days post-challenge (Days 26–46). Results post-vaccination (and pre-challenge) are displayed in Table 2 below. Results post-challenge are displayed in Table 3 below. The results showed that oral administration of each of these two mutants as a vaccine was safe and efficacious against experimentally induced salmonellosis.

TABLE 2

Lack of clinical signs in vaccinates showing the safety of S. choleraesuis vaccine post-vaccination.

| Vaccine | Time | N = | % Mortality | % Morbidity | % Diarrhea Days | % Shedding Days | Ave. Daily Gain |
|---|---|---|---|---|---|---|---|
| None | pre | 8 | 0 | 0 | 0 | 0 | 0.48 |
|  | post |  | 0 | 0 | 3.3 | 0 |  |
| ΔssaC | pre | 8 | 0 | 0 | 3.1 | 0.0 | 0.39 |
|  | post |  | 0 | 0 | 4.0 | 9.7 |  |
| ΔssaJ | pre | 8 | 0 | 0 | 2.1 | 0.0 | 0.38 |
|  | post |  | 0 | 1.6 | 1.9 | 13.5 |  |

TABLE 3

Reduction in clinical signs in vaccinates post-challenge showing the efficacy of S. choleraesuis vaccine.

| Vaccine | N = | % Mortality | % Morbidity | % Diarrhea Days | % Shedding Days | Ave. Daily Gain |
|---|---|---|---|---|---|---|
| None | 8 | 0 | 13.9 | 34.5 | 54.8 | 0.44 |
| ΔssaC | 8 | 0 | 5.2 | 11.1 | 14.4 | 0.69 |
| ΔssaJ | 8 | 0 | 10.7 | 10.7 | 18.3 | 0.61 |

D. Efficacy of a S. dublin ΔssaC or a S. dublin ΔssaJ or a S. dublin ΔssaT Mutant as Vaccines in Cattle (2051-7923-I-MJK-98-004)

The safety and efficacy of a live-attenuated S. dublin ΔssaC or S. dublin ΔssaJ or S. dublin ΔssaT mutant as vaccines was determined in cattle (36 male and female calves, 10–14 days of age at vaccination). Live-attenuated S. dublin strains were revived from stock cultures by streaking onto blood agar. After incubation for 18–24 hr at 37° C., colonies from a heavy growth area were swept with a sterile loop and inoculated into LB broth. After 14 hrs of static incubation at 37° C., 1.0 ml of this culture was used to innoculate 22.5 ml of fresh LB broth in 250 ml sterile polycarbonate Erlenmeyer flasks. After 6 hrs of static incubation at 37° C., 2.5 ml of the resulting undiluted broth culture was added to 3.0 liters of milk replacer for administration to each calf. Dilution and viable plate count on blood agar determined "Numbers of Viable Bacteria" for each strain at the time of preparation. Each vaccine was maintained at room temperature and delivered to animals as soon as possible after preparation (within ~30 minutes). Baseline temperatures and clinical scores (mortality, physical condition, inactivity, diarrhea (fecal score), and shedding of bacteria) were recorded on Days 1–4. The calves were vaccinated orally via the milk replacer on Day 4 with either wild type or a mutant bacteria at a dose of about ~$1\times10^9$ CFUs/calf. For oral vaccination, 1 ml of the lab grown vaccine culture was innoculated in the calf's milk replacer. The number of CFUs/ml was determined as described above in Example 2B. Because each calf consumed its entire amount of milk replacer on the day of vaccination, the number of CFUs per animal was the same as the number of CFUs/ml of culture.

The calves were monitored daily for clinical symptoms (% mortality, physical condition, % inactive days, fecal score, and 5 shedding days) for 28 days post-vaccination (Days 5–32), of which Days 29–32 were considered a baseline before challenge with wild type bacteria. If a calf died during the period of interest, it was assigned a score of "1" for the mortality variable, otherwise, the mortality variable assigned was "0". The physical condition was scored on a scale of 1 to 5, where "1" was a healthy, active animal with normal hair-coat; "2" was a mildly depressed animal that was intermediate in activity and had a rough hair-coat; "3" was a moderately to severely depressed animal that was inactive/lethargic and/or gaunt irrespective of hair-coat; "4" was a moribund animal; and "5" was a dead animal. If a calf died, the physical condition was assigned a "5" for the day of death (or the following day depending on the time of death), and missing values thereafter. The average physical condition was taken as the average of the daily scores within the period of interest for each calf. The average physical scores were then used to calculate the resealed score in the following way: the resealing score=100×(average physical condition score−1)/4. This converts the 1–5 scale into a 0–100 scale. The % inactive days score was determined by calculating the percent of days during the period of interest that a calf had a score of greater than 2 on the physical condition score. The fecal score was scored on a scale of 1–4 where "1" is normal, solid formed or soft with form; "2" is soft unformed; "3" is watery with solid material; and "4" is profuse watery/projectile with little or no solid material. The % shedding days was calculated as the percent of days during the period of interest that a calf had a rectal swab positive for *Salmonella*.

The calves were then challenged with a highly virulent, heterologous wild type *S. dublin*, which was a field isolate obtained from a case of bovine salmonellosis, at 28 days post-vaccination (Day 32). The calves continued to be monitored for clinical symptoms for a further 14 days post-challenge (Days 33–46). Results post-vaccination (and pre-challenge) are displayed in Table 4 below. Results post-challenge are displayed in Table 5 below. Necropsy was performed on Day 46 or at death, and tissue and fecal samples were obtained for culture of the challenge organism. The data from culturing of tissue (>2g) or fecal (>2g) samples showed that there was a reduction of the challenge strain in the tissues from animals vaccinated with the SPI2 mutants compared to the naive controls, and that oral administration of each of these three mutants as a vaccine was safe and efficacious against experimentally induced salmonellosis. Protective effects seen with these SPI2 mutants were better than those observed with Δcya Δcrp mutants.

TABLE 4

Lack of clinical signs in vaccinates showing safety of S. dublin vaccines post-vaccination.

| Vaccine/Strain | Time | N = | Mortality (%) | Physical Condition | % Inactive Days | Fecal Score | % Shedding Days |
|---|---|---|---|---|---|---|---|
| None | pre | 6 | 0 | 0.0 | 0 | 1.2 | 0.0 |
|  | post (1–28) |  | 0 | 0.0 | 0 | 1.1 | 0.0 |
| wild-type | pre | 6 | 0 | 0.0 | 0 | 1.3 | 0.0 |
|  | post (1–28) |  | 16.7 | 5.4 | 5.6 | 1.4 | 64.1 |
| ΔssaC | pre | 6 | 0 | 0.0 | 0 | 1.0 | 0.0 |
|  | post (1–28) |  | 0 | 0.0 | 0 | 1.2 | 9.7 |
| ΔssaJ | pre | 4 | 0 | 0.0 | 0 | 1.0 | 0.0 |
|  | post (1–28) |  | 0 | 2.0 | 2.7 | 1.1 | 13.5 |
| ΔssaT | pre | 6 | 0 | 1.0 | 0 | 1.3 | 0.0 |
|  | post (1–28) |  | 0 | 0.3 | 0 | 1.2 | 22.4 |

TABLE 5

Reduction in clinical signs in vaccinates post-challenge showing the efficacy of S. dublin vaccines.

| Vaccine/Strain | N = | Mortality (%) | Physical Condition | % Inactive Days | Fecal Score | % Shedding Days |
|---|---|---|---|---|---|---|
| None | 6 | 50.0 | 13.9 | 16.4 | 1.8 | 78.5 |
| wild-type | 5 | 0 | 0.0 | 0.0 | 1.2 | 39.5 |
| ΔssaC | 6 | 0 | 0.0 | 0.0 | 1.0 | 39.3 |
| ΔssaJ | 4 | 0 | 0.0 | 0.0 | 1.1 | 19.6 |
| ΔssaT | 6 | 0 | 2.1 | 0.0 | 1.2 | 29.2 |

E. Efficacy of a S. typhimurium ΔssaC or a S. typhimurium ΔssaJ or a S. typhimurium ΔssaT Mutant as Vaccines in Cattle (2051-7923-I-MJK-98-006)

The safety and efficacy of a live attenuated S. typhimurium ΔssaC or S. typhimurium ΔssaJ or S. typhimurium ΔssaT mutant as vaccines was determined in cattle as described above in Example 2D. The results, shown in Tables 6 and 7 below, demonstrated that oral administration of each of these three mutants as a vaccine was safe and efficacious against experimentally induced salmonellosis. Protective effects seen with these SPI2 mutants were better than those observed with ΔrfaK mutants.

TABLE 6

Lack of clinical signs following vaccination showing the safety of S. typhimurium vaccines.

| Vaccine/Strain | Time | N = | Mortality (%) | Physical Condition | % Inactive Days | Fecal Score | % Shedding Days |
|---|---|---|---|---|---|---|---|
| None | pre | 6 | 0 | 0.0 | 0 | 1.0 | 0.0 |
|  | post (1–28) |  | 0 | 0.4 | 0 | 1.4 | 7.6 |
| ΔssaC | pre | 6 | 0 | 0.0 | 0 | 1.0 | 0.0 |
|  | post (1–28) |  | 0 | 0.3 | 0 | 1.3 | 84.8 |
| ΔssaJ | pre | 6 | 0 | 0.0 | 0 | 1.3 | 0.0 |
|  | post (1–28) |  | 0 | 0.0 | 0 | 1.4 | 57.6 |
| ΔssaT | pre | 6 | 0 | 0.0 | 0 | 1.0 | 0.0 |
|  | post (1–28) |  | 0 | 0.0 | 0 | 1.4 | 62.9 |
| wild-type | pre | 6 | 0 | 1.0 | 0 | 1.0 | 0.0 |
|  | post (1–28) |  | 0 | 0.0 | 0 | 1.6 | 58.8 |

TABLE 7

Reduction in clinical signs in vaccinates post-challenge showing the efficacy of S. typhimurium vaccines.

| Vaccine/Strain | N = | Mortality (%) | Physical Condition | % Inactive Days | Fecal Score | % Shedding Days |
|---|---|---|---|---|---|---|
| None | 6 | 100.0 | 50.5 | 73.9 | 3.0 | 100 |
| ΔssaC | 6 | 33.3 | 21.9 | 18.8 | 2.6 | 82.1 |
| ΔssaJ | 6 | 83.3 | 38.6 | 43.1 | 2.8 | 94.0 |
| ΔssaT | 6 | 50.0 | 33.0 | 39.5 | 2.4 | 81.0 |
| wild-type | 6 | 66.7 | 51.8 | 61.0 | 3.1 | 91.7 |

F. Efficacy of a S. dublin ΔssaC or a S. dublin ΔssaC/ΔssaT or a S. dublin ΔssaJ/ΔssaT Mutant or a Combination of S. dublin ΔssaC/ΔssaT with S. typhimurium ΔssaC/ΔssaT as Vaccines in Cattle (2051-7923-I-MJK-99-001)

The safety and efficacy of a live attenuated S. dublin ΔssaC or S. dublin ΔssaC/ΔssaT or S. dublin ΔssaJ/ΔssaT mutant or a combination of S. dublin ΔssaC/ΔssaT with S. typhimurium ΔssaC/ΔssaT as vaccines was determined in cattle as described above in Example 2D. The results, shown in Tables 8 and 9 below, demonstrated that oral administration of each of these three mutants as a vaccine was safe and efficacious against experimentally induced salmonellosis. Results also showed that there was no interference when a combination of S. dublin and S. typhimurium mutants were administered. Animals vaccinated with both S. dublin ΔssaC/ΔssaT and S. typhimurium ΔssaC/ΔssaT vaccine constructs had no mortality and the lowest clinical scores of all groups following challenge-exposure with a highly virulent heterologous S. dublin challenge strain. Because only partial protection to challenge with S. dublin is afforded by vaccination of calves with live attenuated S. typhimurium vaccines, the resistance of these animals was likely due to immunity induced by the S. dublin component of the vaccine. Thus, efficacy of the S. dublin component of the vaccine was not interfered with by the presence of the S. typhimurium component, and it is possible that the latter may actually enhance immunity to S. dublin when given as a combination v

TABLE 8

Lack of clinical signs following vaccination showing the safety of S. dublin single and double-deletion vaccines, and S. dublin/S. typhimurium combination vaccines.

| Vaccine | Time | N = | Mortality (%) | Physical Condition | % Inactive Days | Fecal Score | % Shedding Days |
|---|---|---|---|---|---|---|---|
| None | pre | 6 | 0 | 0 | 0 | 7.5 | 0 |
|  | post (1–28) |  | 16.7 | 2.65 | 3.3 | 17.5 | 0 |
| S dublin ΔssaC/T S typhim. ΔssaC/T | pre | 6 | 0 | 0 | 0 | 7.5 | 0 |
|  | post (1–28) |  | 0 | 0.89 | 0 | 17.5 | 0 |
| S dublin ΔssaC | pre | 6 | 0 | 0 | 0 | 10.0 | 0 |
|  | post (1–28) |  | 0 | 0.15 | 0 | 12.5 | 8.0 |
| S dublin ΔssaC/T | pre | 6 | 0 | 0 | 0 | 0 | 0 |
|  | post (1–28) |  | 0 | 0.89 | 0 | 10.0 | 13.9 |
| S dublin ΔssaJ/T | pre | 6 | 0 | 1.0 | 0 | 1.4 | 8.3 |
|  | post (1–28) |  | 0 | 1.03 | 0 | 1.4 | 26.8 |

TABLE 9

Reduction in clinical signs in vaccinates post-challenge showing the efficacy of S. dublin single and double-deletion vaccines, and S. dublin/S. typhimurium combination vaccines.

| Vaccine | N = | Mortality (%) | Physical Condition | % Inactive Days | Fecal Score | % Shedding Days |
|---|---|---|---|---|---|---|
| None | 6 | 100.0 | 36.1 | 33.2 | 50.0 | 100.0 |
| S. dublin ΔssaC/T S. typhim ΔssaC/T. | 6 | 0 | 10.0 | 2.8 | 27.5 | 68.6 |
| S. dublin ΔssaC | 6 | 16.7 | 12.4 | 11.6 | 22.5 | 75.0 |
| S. dublin ΔssaC/T | 6 | 20.0 | 12.7 | 14.8 | 20.0 | 78.6 |
| S. dublin ΔssaJ/T | 6 | 16.7 | 17.6 | 23.7 | 27.5 | 83.3 |

G. Efficacy of a S. typhimurium ΔssaC or a S. typhimurium ΔssaC/ΔssaT or a S. typhimurium ΔssaJ/ΔssaT Mutant or a Combination of S. dublin ΔssaC/ΔssaT with S. typhimurium ΔssaC/ΔssaT as Vaccines in Cattle (2051-7923-I-MJK-99-007)

The safety and efficacy of a live attenuated S. typhimurium ΔssaC or S. typhimurium ΔssaC/ΔssaT or S. typhimurium ΔssaJ/ΔssaT mutant or a combination of S. dublin ΔssaC/ΔssaT with S. typhimurium ΔssaC/ΔssaT as vaccines was determined in cattle challenged with virulent S. typhimurium as described above in Example 2D. The results, shown in Tables 10 and 11 below, demonstrated that oral administration of each of these three mutants as a vaccine was safe and efficacious against experimentally induced salmonellosis. As described above in Example 2F, these results also showed that there was no interference when a combination of S. dublin and S. typhimurium were administered.

TABLE 10

Lack of clinical signs following vaccination showing the safety of S. typhimurium vaccines.

| Vaccine | Time | N = | Mortality (%) | Physical Condition | % Inactive Days | Fecal Score | % Shedding Days |
|---|---|---|---|---|---|---|---|
| None | pre | 6 | 0 | 0 | 4.2 | 0 |  |
|  | post (1–28) |  | 0 | 0.45 | 0 | 0 |  |
| S dublin ΔssaC/T S typhim ΔssaC/T. | pre | 6 | 0 | 0 | 0 | 0 |  |
|  | post (1–28) |  | 0 | 0 | 0 | 61.4 |  |
| S typhim ΔssaC | pre | 6 | 0 | 0 | 8.3 | 0 |  |
|  | post (1–28) |  | 0 | 0 | 0.6 | 71.4 |  |
| S typhim ΔssaC/T | pre | 6 | 0 | 0 | 4.2 | 0 |  |
|  | post (1–28) |  | 0 | 0 | 0 | 76.2 |  |
| S typhim ΔssaJ/T | pre | 6 | 0 | 0 | 4.2 | 0 |  |
|  | post (1–28) |  | 0 | 0.74 | 0 | 71.2 |  |

TABLE 11

Reduction in clinical signs in vaccinates post-challenge showing the efficacy of S. typhimurium vaccines.

| Vaccine | N = | Mortality (%) | Physical Condition | % Inactive Days | Fecal Score | % Shedding Days |
|---|---|---|---|---|---|---|
| None | 6 | 100.0 | 36.98 | 32.6 | 77.5 | 100.0 |
| S. dublin ΔssaC/T S. typhim ΔssaC/T. | 6 | 16.7 | 11.11 | 1.4 | 25.0 | 82.2 |
| S. typhim ΔssaC | 6 | 33.3 | 11.61 | 7.1 | 30.0 | 92.4 |
| S. typhim ΔssaC/T | 6 | 0 | 9.23 | 5.6 | 22.5 | 86.9 |
| S. typhim ΔssaJ/T | 6 | 16.7 | 18.4 | 18.4 | 30.0 | 79.0 |

Numerous modifications and variations of the above-described invention are expected to occur to those of skill in the art. Accordingly, only such limitations as appear in the appended claims should be placed thereon.

What is claimed is:

1. A vaccine composition comprising an immunologically protective amount of a first attenuated, non-reverting mutant *Salmonella* bacterium in which the ssaT and ssaJ genes have been inactivated,
wherein said ssaT gene comprises the nucleic acid sequence of SEQ ID NO: 1 or 2, and wherein said ssaC gene comprises the nucleic acid sequence of SEQ ID NO: 5 or 6.

2. A vaccine composition comprising an immunologically protective amount of a first attenuated, non-reverting mutant *Salmonella* bacterium in which the ssaT and ssai genes have been inactivated;

wherein said ssaT gene comprises the nucleic acid sequence of SEQ ID NO: 1 or 2, and where said ssaJ gene comprises the nucleic acid sequence of SEQ ID NO: 3 or 4.

3. A vaccine composition of claim 1 further comprising a second attenuated *Salmonella* bacterium in which one or more genes within the SPI2 region have been inactivated wherein said genes are selected from the group consisting of ssaT, ssaJ, ssaC, and ssaM and wherein, said ssaT gene comprises the nucleic acid sequence of SEQ ID NO: 1 or 2, said ssaJ gene comprises the nucleic acid sequence of SEQ ID NO: 3 or 4, said ssaC gene comprises the nucleic acid sequence of SEQ ID NO: 5 or 6, and said ssaM gene comprises the nucleic acid sequence of SEQ ID NO: 7 or 30.

4. A vaccine composition of claim 2 further comprising a second attenuated *Salmonella* bacterium in which one or more genes within the SPI2 region have been inactivated wherein said genes are selected from the group consisting of ssaT, ssaJ, ssaC, and ssaM and wherein, said ssaT gene comprises the nucleic acid sequence of SEQ ID NO: 1 or 2, said ssaJ gene comprises the nucleic acid sequence of SEQ ID NO: 3 or 4, said ssaC gene comprises the nucleic acid sequence of SEQ ID NO: 5 or 6, and said ssaM gene comprises the nucleic acid sequence of SEQ ID NO: 7 or 30.

5. Vaccine of any one of claims 1, 2, 3 and 4, wherein said genes are inactivated by deletion of a portion of the coding region of the gene.

6. A vaccine composition of any one of claims 1, 2, 3 and 4, wherein said first attenuated mutant *Salmonella* bacteria are selected from the group consisting of *S. dublin*, *S. choleraesuis*, *S. typhimurium*, and *S. newport*.

7. A vaccine composition of claim 3 or 4, wherein said first and second attenuated mutant *Salmonella* bacteria are selected from the group consisting of *S. dublin*, *S. choleraesuis*, *S. typhimurium*, and *S. newport*.

* * * * *

UNITED STATES PATENT AND TRADEMARK OFFICE
CERTIFICATE OF CORRECTION

PATENT NO.     : 6,923,957 B2
DATED          : August 2, 2005
INVENTOR(S)    : David E. Lowery and Michael J. Kennedy It is certified that error appears in the above-identified patent and that said Letters Patent is hereby corrected as shown below:

Column 37,
Line 49, "ssaJ" should read -- ssaC --.
Line 57, "ssai" should read -- ssaJ --.

Signed and Sealed this

Seventh Day of February, 2006

JON W. DUDAS
*Director of the United States Patent and Trademark Office*